(12) United States Patent
Yang et al.

(10) Patent No.: US 6,896,780 B2
(45) Date of Patent: May 24, 2005

(54) MICROELECTRODE, MICROELECTRODE ARRAY AND METHOD FOR MANUFACTURING THE MICROELECTRODE

(75) Inventors: Hae Sik Yang, Daejon-Shi (KR); Chi Hoon Jun, Daejon-Shi (KR); Chang Auck Choi, Daejon-Shi (KR); Youn Tae Kim, Daejon-Shi (KR)

(73) Assignee: Electronics and Telecommunications Research Institute (KR)

( * ) Notice: Subject to any disclaimer, the term of this patent is extended or adjusted under 35 U.S.C. 154(b) by 467 days.

(21) Appl. No.: 10/020,774

(22) Filed: Dec. 11, 2001

(65) Prior Publication Data

US 2003/0047450 A1 Mar. 13, 2003

(30) Foreign Application Priority Data

Sep. 12, 2001 (KR) ........................................ 2001-56159

(51) Int. Cl.[7] ........................ G01N 27/28; G01N 27/327
(52) U.S. Cl. .............. 204/408; 204/403.01; 204/403.14
(58) Field of Search ................................. 204/408, 424, 204/425, 403.01, 403.04, 403.13, 403.14

(56) References Cited

U.S. PATENT DOCUMENTS

| | | | |
|---|---|---|---|
| 5,296,408 A | 3/1994 | Wilbarg et al. ............. | 437/203 |
| 5,605,662 A | 2/1997 | Heller et al. ................ | 422/68.1 |
| 5,849,486 A | 12/1998 | Heller et al. .................... | 435/6 |
| 5,907,765 A | 5/1999 | Lescouzeres et al. .......... | 438/49 |
| 5,948,361 A | 9/1999 | D'Aragona et al. .......... | 422/98 |
| 6,017,696 A | 1/2000 | Heller ............................ | 435/6 |
| 6,023,091 A | 2/2000 | Koch et al. ................. | 257/536 |
| 6,093,302 A | 7/2000 | Montgomery ............... | 205/122 |
| 6,136,212 A | 10/2000 | Mastrangelo et al. | |
| 6,340,419 B1 * | 1/2002 | Nakae et al. ............... | 204/429 |

OTHER PUBLICATIONS

Electroanalysys 1999, 11, No. 4, pp. 223–228.
Journal of Electroanalytical Chemistry 492 (2000), pp. 150–155.
IEEE Journal of Microelectromechanical Systems, vol. 8, no. 2, Jun. 1999, pp. 135–145.
Sensors and Actuators 76 (1999), pp. 356–364.
Biosensors & Bioelectronics 14 (1999), pp. 443–456.

* cited by examiner

Primary Examiner—Alex Noguerola
(74) Attorney, Agent, or Firm—Blakely Sokoloff Taylor & Zafman

(57) ABSTRACT

The present invention relates to a microelectrode, a microelectrode array, and a method of manufacturing the microelectrode of which temperature can be controlled. The microelectrode comprises a sealed cavity formed in a silicon substrate for thermal isolation, a microheater formed on the sealed cavity, and an electrode heated indirectly by the microheater. According to the present invention, it is possible to manufacture with CMOS process the microelectrode and the microelectrode array which have excellent electric insulation and thermal isolation between a microheater and a silicon substrate, which has a small power consumption, which has high heating and cooling speed and which has no corrosion.

13 Claims, 17 Drawing Sheets

MICROELECTRODE, MICROELECTRODE ARRAY AND METHOD FOR MANUFACTURING THE MICROELECTRODE

BACKGROUND OF THE INVENTION

1. Field of the Invention

The present invention relates to a microelectrode, and a microelectrode array of which temperature can be controlled in a solution, and in particular, to the microelectrode and the microelectrode array which have excellent thermal isolation between a microheater and a substrate, which has a small power consumption for heating, which has high heating and cooling speed and which can be manufactured by semiconductor manufacturing process.

2. Disclosure Statement

Presently, researches have been vigorously performed about the microelectrode of which the potential of the electrode can be adjusted in a state where the microelectrode is dipped in a solution. Such a microelectrode can not only be used as a measuring electrode of an electrochemical sensor, but also be used in site-selectively obtaining a micropattern or in controlling an interaction or transport of a biomolecule by controlling the potential of the microelectrode.

Now, review will be done on concrete examples in which the microelectrode is applied to the electrochemical measurement, micropatterning and control of the biomolecule.

As interest in personal health and environment has been increased, development of small sensors which can obtain various precise information in short period of time is required. In particular, development of sensors using the microelectrode and electrochemical measurement method is required to miniaturize these sensors. As electrochemical sensors using the microelectrode, there are electrochemical biosensor using an enzyme and a potentiometric sensor which measures pH or concentration of ions from a potential difference. Recently, electrochemical DNA sensors and electrochemical immunosensors using the microelectrode are manufactured, too.

The electrode array in which there are many number of microelectrodes in a substrate are applied to an electrochemical DNA chip, an electrochemical protein chip and an electronic tongue, etc. in which multiple processes can be performed parallel.

In addition, the microelectrode composed of interdigitated array (IDA) structure can be used in measuring a change of electrode surface from impedance or in improving sensitivity by amplifying the electrode reaction. In case of bonding or integrating the microelectrode with fluid control devices, it can be possible to construct a lab-on-a-chip in which separation, reaction and detection can be performed in a single chip.

Generally, micropattern can be manufactured by the semiconductor manufacturing process such as deposition, photolithography and etching, or by electrodeposition. In case of using the electrodeposition process, not only metals such as copper but also conducting polymer and metal oxide having electric conductivity can be site-selectively deposited. If electrodeposition is performed on the microelectrode, the micropattern of the metal, polymer and metal oxide can be obtained with ease.

Recently, many attempts have been trying to site-selectively immobilize the biomolecule on the electrode by voltage control (Cosnier, Serge, "Biomolecule immobilization on electrode surfaces by entrapment or attachment to electrochemically polymerized films. A review" Biosensors & Bioelectronics 14: pp. 443–456 (1999)). A method of site-selectively electropolymerizing biomolecule-attached monomer on the microelectrdode, or site-selectively forming the biomolecule-entrapped polymer on the microelectrode in a solution containing monomer and biomolecule has been developed. Also developed is a method by Nanogen Company in which DNA immobilization is controlled by electrode potential (refer to U.S. Pat. No. 5,605,662). Since DNA has negative(−) charge, it moves to the electrode if positive voltage is applied to the electrode. At this time, the moved DNA is immobilized on the electrode surface. Eventually, DNA is site-selectively immobilized on the electrode by potential control.

In addition, a method of site-selectively immobilizing the biomolecule by electrochemically changing the pH around the electrode has been developed. Combimetrix Company suggested a method of site-selectively synthesizing an oligonucleotide to the microelectrode by using such concept. (U.S. Pat. No. 6,093,302).

Since the biomolecule such as DNA or protein has multiple electric charges, the transport or interaction of DNA and protein can be controlled by potential control. Nanogen Company has been accomplished that positive potential is applied to the microelectrode immobilized with single-strand DNA so that the single-strand DNA which is complementary to the DNA is hybridized in short time(U.S. Pat. No. 5,849,486). DNA in which bases of two single-strand DNA are not completely complement is dehybridized by applying the negative potential to the microelectrode (U.S. Pat. No. 6,017,696).

As described above, electrochemical measurement of biomolecule, micropatterning of biomolecule and control of biomolecule can be done by potential control of the microelectrode. However, to manufacture an electrode having better performance, the potential control of the electrode as well as temperature control is necessary. A research on the electrode of which temperature control is possible is mainly performed by Gründler Group (Gründler, Peter, et al., "The technology of hot-wire electrochemistry", Electroanalysis 11: pp. 223–228(1999)). It is expected that the micropatterning of biomolecule and the control of biomolecule in addition to the electrochemical measurement of biomolecule will be possible by adjusting the temperature of electrode in the same way as in the case of the potential control.

In terms of electrochemistry, when temperature of the electrode is varied, the electrochemical kinetics, mass transport and electrochemical thermodynamics are influenced. The electrochemical kinetics increases exponentially with temperature, and the transport of material around electrode occurs vigorously due to heat convection. Therefore, the current increases according to the increase in temperature, which can be used in raising the sensitivity of an electrochemical sensor. If the temperature changes, redox potential associated with electrochemical thermodynamics changes too, and the temperature changes of the electrode surface can be indirectly measured from the changes of the redox potential.

The reaction and interaction control of biomolecule is possible to some degree by adjusting the temperature because biomolecule is very sensitive to temperature. The activity of biomolecule such as enzyme increases with temperature. Since the activity of biomolecule can be easily lost if the high temperature is maintained for long period, therefore, appropriate temperature control is necessary according to each biomolecule. An example of the control of biomolecule using temperature control is adjustment of DNA hybridization/dehybridization. When the temperature rises, the dehybridization of DNA occurs, and when the temperature falls, the hybridization of DNA occurs again. If dehybridization/hybridization is repeated while cloning the DNA of desired part at the time of dehybridization, it is possible to amplify DNA in great amount in short period. At this time, precise temperature adjustment and rapid heating and cooling are indispensable for rapid and precise amplification.

If the temperature control of the electrode is possible when the biomolecule is immobilized on the electrode surface, the biomolecule can be effectively controlled. The redox reaction and the micropatterning are highly influenced by temperature of the electrode surface. Therefore, it is not necessary to heat up the solution entirely but only to heat up the electrode surface for such control. It is effective only to heat the electrode surface or the surroundings of the electrode for rapid heating and cooling. Even if the electrode is only heated, if the volume of the solution is extremely small, the temperature control of the solution is possible by heating the microelectrode alone.

If a large amount of electric power is consumed in adjusting the temperature, a large battery or power source is required even if the volume of the electrode and measurement circuit is small. Eventually, entire size of the small measurement system depends on the size of battery or power source. Therefore, to manufacture the small sensor, the temperature-controllable electrode with small power consumption must be used.

Since the size of the microelectrode can be decreased to a very small size if the semiconductor manufacturing process is used, the electric power required to increase the temperature of the electrode surface is not large. Even in a solution of large heat capacity, if the size of the electrode is small, the electrode surface can be rapidly heated. Also, since the convection layer of the solution caused by the heat is not large, when the heating is interrupted, the temperature of the electrode falls down to the temperature of surroundings in short period.

As described above, the temperature control of the electrode can be applied to electrochemical measurement and control of biomolecule, and for this, it is required above all to use the microelectrode of precise temperature control and high speed of heating and cooling. Now, conventional technologies for adjusting the temperature of the electrode will be reviewed below.

The mostly frequently used method in adjusting the temperature of the electrode is a method in which the solution is entirely heated or cooled thereby raising or lowering the temperature of the electrode. However, this method has many disadvantages that since in that method the solution is entirely heated, it takes long time to raise or lower temperature, and it is difficult to maintain entirely the temperature of the solution constant.

There is also a method in which the electrode is heated by radiation. One example is to instantaneously heat the electrode by shooting the laser to the front surface or back surface of the electrode. This method is frequently used in checking the change with time after instantly heating the electrode. However, this method has the problems that it is difficult to maintain the temperature of the electrode and the device is expensive and the entire volume is large since laser is used. There is also a method of heating the electrode with the light produced from the tungsten lamp. However, this method has difficulty in efficiently adjusting the temperature, too.

Recently, a method of directly heating the electrode by Joule heating is also used (Gründler, Peter, et al., "The technology of hot-wire electrochemistry", Electoanalysis 11: pp. 223–228 (1999)). This is a method of heating the electrode by applying high frequency alternating current of about 100 kHz to the electrode. However, this method has problem that electric power consumption is large, and the redox current can be influenced by the alternating current. Furthermore, there are problems that since the alternating current of high frequency is used, an expensive alternating current generator is necessary, and large power is consumed. In addition, since the resistance of the wiring which connects the electrode to the external circuit is larger than that of the electrode in case of manufacturing the microelectrode in silicon substrate, there is a great possibility that most of electric power is consumed in the wiring than in the electrode. Therefore, this method can not be used in manufacture of the microelectrode.

Heating by RF(radio frequency) radiation is reported as a method of heating by inducing eddy current to the metal electrode, however, this method has problem that electric power consumption is serious and miniaturization is difficult, too (Qiu, Fulian, et al. "Thermal activation of electrochemical processes in a RF-heated channel flow cell: experiment and finite element simulation", Journal of Electroanalytical Chemistry 491: pp. 150–155 (2000)).

A method of indirectly heating the electrode by a microheater is used too. In this method, heat generated from Joule heating in the microheater is transferred to the electrode through a medium to heat the electrode. Since voltage or current must be applied to the microheater for Joule heating, the microheater must be electrically insulated from the electrode. To make the heat generated from Joule heating to be effectively transferred to the electrode, there must be no material of high heat conductivity around the microheater. A silicon substrate of very high heat conductivity is mainly used for semiconductor device manufacturing. In case where the microheater exists on the silicon substrate, substantial amount of heat generated at the microheater is not transferred to the electrode but leaks out to the silicon substrate. To reduce such heat loss, a method of forming an etched pit on the silicon substrate around the microheater or forming a cavity between silicon substrate and the heater is used.

Indirect heating of the microelectrode with the microheater is substantially effective in view of power consumption or applicability to a sensor among the methods of adjusting the temperature of the electrode as described above. Formation of the etched pit or the cavity for reducing heat loss of the microheater can be implemented by micromachining technology. The micromachining technology can be classified into bulk micromachining for machining upper and lower surfaces of the silicon substrate and surface machining for stacking a thin film on top of the substrate, etching and machining the thin film.

The bulk micromachining is a method of removing silicon from the surroundings of the microheater by etching from a defined area of upper or lower surface. Electric heat loss can be substantially decreased by making a structure of bridge, cantilever and membrane separated from the substrate by forming the etched pit or cavity on the substrate, by using such a method and thereafter forming the microheater. In this case, the manufacturing is easy, however, there is a limit in decreasing the heat loss since it can not essentially remove the air existing in the etched pit or cavity. In addition, the method has a disadvantage that the structure cannot be manufactured with the standard CMOS process.

The surface micromachining is a method of forming a microcavity by etching a sacrificial layer formed on a top surface, and forming the microheater on the cavity. This method has an advantage of manufacturing with the standard CMOS process, and making a microcavity array with ease. However, there is no report so far of the microelectrode in which the temperature can be adjusted in solvent by using the surface micromachining.

When using the microelectrode having a cavity in solution, there is a problem that the solution enters into the cavity so that the electric heat loss of the microheater becomes large. Therefore, the cavity of the microelectrode to be used in the solution must be sealed. In case this cavity is sealed under vacuum, the heat loss of the microheater becomes very small.

In a method of manufacturing a structure having a cavity on a silicon substrate by using the surface micromachining, conventional technology status disclosed as references or patents will be reviewed below.

First, U.S. Pat. No. 6,023,091 discloses a structure in which a cavity and microheater are formed on a silicon substrate, where the cavity is formed by depositing and etching a sacrificial layer without etching the silicon substrate. The manufacturing process is simple, however, there is a disadvantage that effective thermal isolation cannot be obtained since the depth of cavity cannot be made large.

In U.S. Pat. No. 5,948,361, a substrate A formed with microheater is junctioned to a substrate B formed with cavity, and then the substrate A is removed leaving the microheater. This method has a problem that it is difficult to align and junction the two substrates.

U.S. Pat. No. 5,907,765 discloses a method comprising the steps of: forming an insulation film on a silicon substrate; etching the silicon substrate in a portion to be used as a cavity; filling a sacrificial layer; forming a heater film; etching the sacrificial layer through an etching channel; and sealing the etching channel. There is a problem that in the step of filling the sacrificial layer after etching the silicon substrate, it is difficult to form the sacrificial layer thick and to a desired shape. That is, a sealed cavity with excellent thermal isolation performance cannot be obtained.

U.S. Pat. No. 5,296,408 discloses a method comprising the steps of: etching a silicon substrate; filling aluminum, depositing a silicon oxide film $SiO_2$; and producing a sealed cavity in the place where aluminum was by diffusing the aluminum with heat.

Reference (Liu, Chang et al., "Sealing of micromachined cavities using chemical vapor deposition methods: characterization and optimization" 8: pp. 135–145 (1999)) discloses a method comprising the steps of: defining a silicon nitride film $Si_3N_4$ on the silicon surface; forming a thermal oxide sacrificial layer by thermal oxidizing the surface of a portion where silicon is exposed; forming a sacrificial layer to be used as etching path; forming a supporting film from the silicon nitride film, forming a cavity by forming an etching hole and thereafter etching the sacrificial layer; and sealing the etching hole under vacuum. Since the cavity is vacuum-sealed cavity, in case where the microheater exists on the sealed cavity, it can obtain good thermal isolation. However, since the depth of sealed cavity has to be made within 1 to 2 μm, there is a limit in making the thermal isolation performance excellent.

A good deal of researches on formation of an efficient sealed cavity has been performed as seen in the patent and references stated above, however, a good deal of rooms are left to improve the thermal isolation. In particular, a development of sealed cavity is necessary which can have excellent thermal isolation performance by making the depth of sealed cavity large.

On the other hand, in case of microelectrode which is used in solution and heated indirectly with microheater, following problems exist in insulation between a microheater and an electrode, corrosion of wirings, and resistance of wirings as well as a sealed cavity with good thermal isolation.

In case of heating the electrode with heat produced by applying voltage or current to microheater, and measuring the redox current flowing to the electrode, the voltage or current of the microheater can influence current of the electrode. For example, if the difference of voltages each applied to the microheater and the electrode is 1 V, and resistance of an insulation film between the microheater and the electrode is 1 GΩ, then, current of 1 nA can flow between the microheater and the electrode. Since this amount of current can influence the redox current, the insulation performance of the insulation film must be very good. In particular, the insulation performance of the insulation film is far more important when applying high voltage to the microheater to increase the temperature of the electrode.

Corrosion of wirings can be another problem in the microelectrode which can adjust the temperature in solution. There are many cases where the solution in which the microelectrode is to be dipped has high concentration ion (especially, chlorine ion), in general, aluminum used in wirings in semiconductor manufacturing process is corroded with ease in the solution. The corrosion can be reduced substantially if a protection film is formed on metal wirings, however, in case there are many pin holes in the protection film, the corrosion of metal wirings can easily arise. Since the protection film consisting of a silicon oxide film or a silicon nitride film is formed with PECVD (low pressure chemical vapor deposition) in the low temperature under the condition that the metal wirings are formed, there are many pin holes in the film.

Voltage or current is applied to heat the microheater, where if the voltage or current applied to resistor changes, temperature of the electrode changes. The resistance of microheater must be uniform to have same temperature performance regardless of the electrode when same voltage is applied, and resistance of wirings connecting the microheater must be very small in comparison to that of the microheater. Since the number of necessary wirings and the area of wirings are increased in case of making a microelectrode array, the line width of wirings must be decreased. Since the resistance of wirings increases if the line width is decreased, metal of low specific resistivity must be used to lower the resistance of wirings. Generally, aluminum widely used as wirings has large specific resistivity and a thick film can be deposited with aluminum with inexpensive cost, and a micropattern can be obtained with aluminum, however, there is a disadvantage that aluminum is corroded easily in solution. Another metal that can be used as wirings in a CMOS process is platinum, however, since platinum has high specific resistivity, a platinum film must be formed thick to reduce the resistance. In this case, it costs high expense and it is difficult to form micropattern with dry or wet etching. Therefore, there is a limit in using the platinum as wirings of a microheater. In case of gold, although it has low specific resistivity, since the standard CMOS process cannot be performed after deposition, it cannot be used as wirings. Metals such as silver, copper, etc. having small specific resistivity are not easily used in general semiconductor manufacturing process.

It is required to manufacture a microelectrode having adjustable temperature in the solution to apply the microelectrode to electrochemical measurement of biomolecule, micropatterning of biomolecule and control of biomolecule as described above.

SUMMARY OF THE INVENTION

Therefore, an object of the invention is to provide a structure of a microelectrode and a microelectrode array which have small electric power consumption, and can be rapidly heated and cooled in short time.

A microelectrode of the present invention to accomplish the object described above is characterized in that it comprises a substrate having a trench; a support film formed on the substrate so that a cavity is formed in the trench; a sealing film formed on the support film to seal the cavity; a microheater formed on the sealing film, with the microheater being composed of resistor which can diffuse heat; an insulation film formed on the entire structure including the microheater; a plurality of wirings formed on portions of the insulation film and connected to the microheater through contact holes; an electrode formed on a portion of the insulation film and indirectly heated by the microheater; and a protection film formed on the entire structure including the electrode and wirings, and patterned to expose a portion of the electrode and wirings.

A microelectrode array of the present invention is characterized in that a plurality of microelectrodes each comprising a substrate having a trench; a support film formed on the substrate so that a cavity is formed in the trench; a sealing film formed on the support film to seal the cavity; a microheater formed on the sealing film, with the microheater being composed of resistor which can diffuse heat; an insulation film formed on the entire structure including the microheater; a plurality of wirings formed on portions of the insulation film and connected to the microheater through contact holes; an electrode formed on a portion of the insulation film and indirectly heated by the microheater; and a protection film formed on the entire structure including the electrode and wirings, and patterned to expose a portion of the electrode and wirings; are arranged in a shape of array, and in that said microelectrode array is constructed so that the wirings connected to each microheater are respectively connected to wiring and pad of microheater or independently connected to each pad.

The present invention is characterized in that the support film is composed of one of polysilicon and silicon nitride film and in that the sealing film, insulation film and protection film are composed of one of silicon oxide film and silicon nitride film.

The present invention is characterized in that the insulation film is composed of stacking of LPCVD silicon oxide film, LPCVD silicon nitride film and LPCVD silicon oxide film, and the protection film is composed of stacking of PECVD silicon oxide film, PECVD silicon nitride film and PECVD silicon oxide film.

The present invention is characterized in that the microheater is composed of one of platinum and doped polysilicon, the inside of said cavity is maintained to be vacuum, said electrode is formed of one of platinum and material including platinum, and said electrode is formed as IDA structure.

The present invention is characterized in that the electrode is formed with metal electrode on top of it, the metal electrode is formed as IDA structure, and area of the metal electrode is larger than that of the cavity.

The present invention is characterized in that the number of electrodes that the each microelectrode has is one or more, and on top of the plurality of electrodes is formed one metal electrode.

The present invention is characterized in that the protection film is patterned so that the electrode is less exposed than the area of the cavity, and the wiring is formed of one of aluminum and material including aluminum.

In addition, a method of manufacturing a microelectrode of the present invention is characterized in that it comprises the steps of forming a thermal oxide prevention film on a silicon substrate; forming a trench array composed of a plurality of trenches by patterning the thermal oxide protection film and thereafter etching silicon substrate of exposed portion; proceeding a thermal oxidation process so that a first sacrificial layer is formed in the trench; forming a second sacrificial layer on the silicon substrate including the first sacrificial layer after removing the thermal oxidation prevention film; forming an etching hole so that both sides of the second sacrificial layer are exposed by forming a support film on entire upper surface and then patterning it; forming a cavity on the silicon substrate by removing the first and second sacrificial layers through the etching hole; forming a sealing film on the support film so as to seal the cavity; forming a microheater composed of resistor which can diffuse heat on the sealing film on top of said cavity; forming a contact hole so as to expose predetermined portion of the microheater by forming an insulation film in entire upper surface and thereafter patterning it; forming a plurality of wirings connected to the microheater through the contact hole on the insulation film; forming an electrode on the insulation film on top of the microheater; and exposing predetermined portion of the wirings and electrode by forming a protection film in entire upper surface and thereafter patterning it.

The present invention is characterized in that the wiring and electrode are formed at the same time, the thermal oxidation protection film is composed of silicon nitride film, and the second sacrificial layer is composed of low temperature silicon oxide film.

The present invention is characterized in that a micro porosity is formed in each trench at the thermal oxidation process, and the first and second sacrificial layers are removed by one of HF solvent and mixture gas of anhydrous HF and $CH_3OH$.

The present invention is characterized in that it further comprises the step of doping the silicon substrate of trench array to increase thermal oxidation rate from the step of forming the trench array.

The present invention is characterized in that it further comprises the step of planarising the surface by chemical/mechanical polishing from the step of forming the second sacrificial layer.

The present invention is characterized in that it further comprises the step of high temperature treatment to reduce the strain of thin film from the step of forming the support film.

The present invention is characterized in that it further comprises the step of forming metal electrode on top of the electrode.

BRIEF DESCRIPTION OF THE DRAWINGS

The above and other objects, effects, features and advantages of the present invention will become more apparent by describing in detail the preferred embodiment of the present invention with reference to the attached drawings in which:

FIGS. 2b to 2d are sectional views to illustrate FIG. 2a;

FIGS. 3b and 3c are sectional views to illustrate FIG. 3a;

FIG. 4b is a sectional view to illustrate FIG. 4a;

FIG. 5b is a sectional view to illustrate FIG. 5a;

FIG. 6b is a sectional view to illustrate FIG. 6a;

FIG. 7b is a sectional view to illustrate FIG. 7a;

Similar reference characters refer to similar parts in the several views of the drawings.

DETAILED DESCRIPTION OF THE INVENTION

The objects and various advantages of the present invention will be clearer to the person having ordinary skill in this field with reference to the accompanying drawings and preferable embodiments described below.

The embodiments of the present invention will be explained in detail below with reference to the accompanying drawings.

Figure 1A:
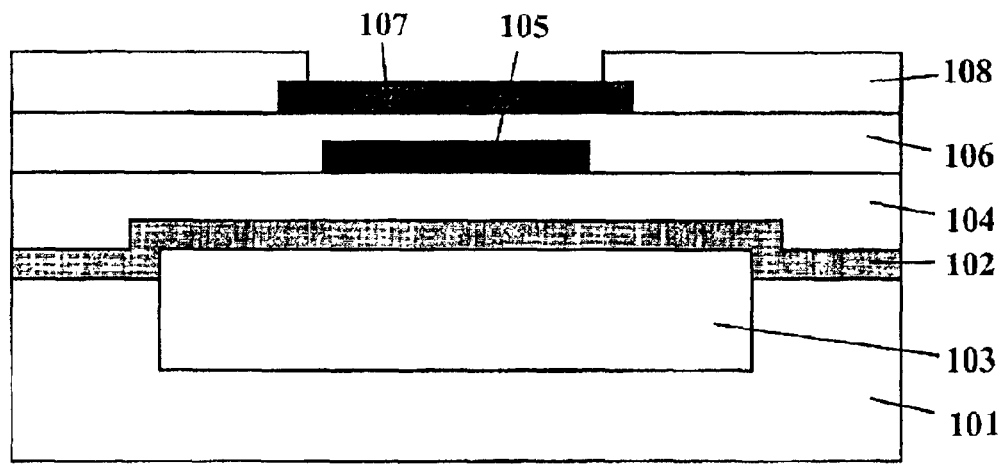
FIGS. 1a and 1b are sectional views to illustrate a microelectrode according to the present invention.
Figure 1B:
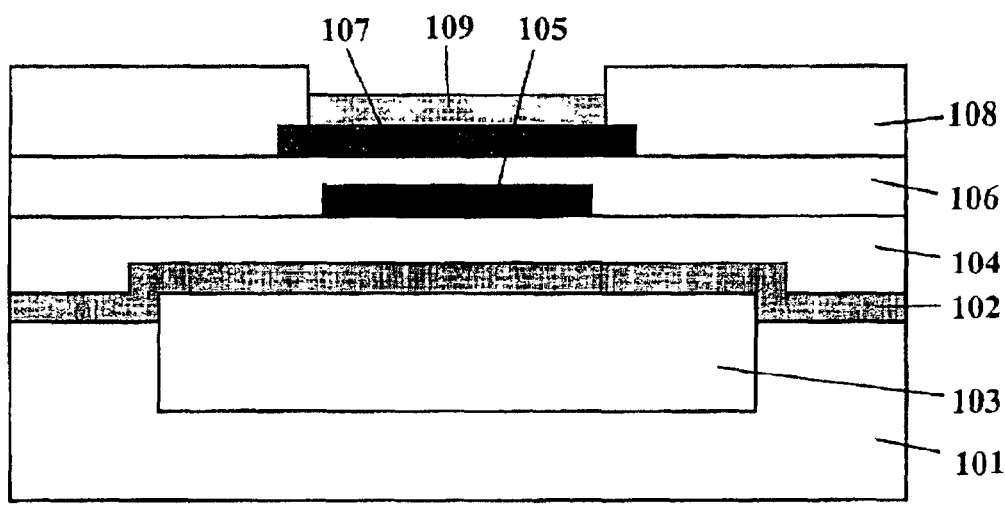

FIGS. 1a and 1b are sectional views of a microelectrode according to the present invention where temperature adjustment is possible in solution.

The microelectrode is composed of a sealed cavity 103 for minimizing the heat loss to the silicon substrate 101, a support film 102 for supporting the sealed cavity 103, a sealed film 104 for sealing the cavity, a microheater 105 formed on the sealed cavity 103 and composed of a resistor which can diffuse heat, an insulation film 106 for electrical insulation of the microheater 105 and an electrode 107, the electrode 107 formed on the insulation film 106, a protection film 108, and a metal electrode 109 formed on the electrode 107.

FIG. 1a is a sectional view of a microelectrode having a structure in which the electrode 107 contacts the solution, and FIG. 1b is a sectional view of a microelectrode having a structure in which the metal electrode 109 contacts the solution, where the metal electrode 109 is formed on the electrode 107.

FIGS. 2a to 7b are sectional views and plan views of microelectrodes having a basic structure of FIG. 1 and having a deep sealed cavity, wirings, pad, etching hole, contact hole, and etc.

The microelectrode is comprised of silicon substrates 201, 301, 401, 501, 601 and 701, sealed cavities 203, 303, 403, 503, 603 and 703 for thermal isolation, support films 202, 302, 402, 502, 602 and 702 for supporting the sealed cavities 203, 303, 403, 503, 603 and 703, etching holes 209, 309, 409, 509 and 609 through which the etching solution flows through at the time of etching the sacrificial layers existing in the sealed cavities 203, 303, 403, 503, 603 and 703, the sealing films 204, 304, 404, 504, 604 and 704 for sealing the etching holes 209, 309, 409, 509 and 609, microheaters 205, 305, 405, 505, 605 and 705 composed of resistors which can diffuse the heat, insulation films 206, 306, 406, 506, 606 and 706 for electrical insulation between the microheaters 205, 305, 405, 505, 605 and 705 and electrodes 207, 307, 407, 507, 607 and 707, the electrodes 207, 307, 407, 507, 607 and 707 formed on the insulation film, contact holes 210, 310, 410, 510 and 610 for connecting the microheaters 205, 305, 405, 505, 605 and 705 and wirings 211, 311, 411, 511, 611 and 710, the wirings 211, 311, 411, 511, 611 and 710 for connecting the microheaters 205, 305, 405, 505, 605 and 705 and pads 212, 312, 313, 412, 512, 612 and 711, protection films 208, 308, 408, 508, 608 and 708 for protecting a portion of the electrodes 207, 307, 407, 507, 607 and 707, and wirings 211, 311, 411, 511, 611 and 710, pads 212, 312, 412, 512, 612 and 712 for connection with external circuit, and metal electrodes 613 and 709.

In FIGS. 2a to 5b, the metal electrode does not exist, however, there can be a structure in which the metal electrode 109 exists on the electrode 107 as in FIG. 1b.

Figure 2A:
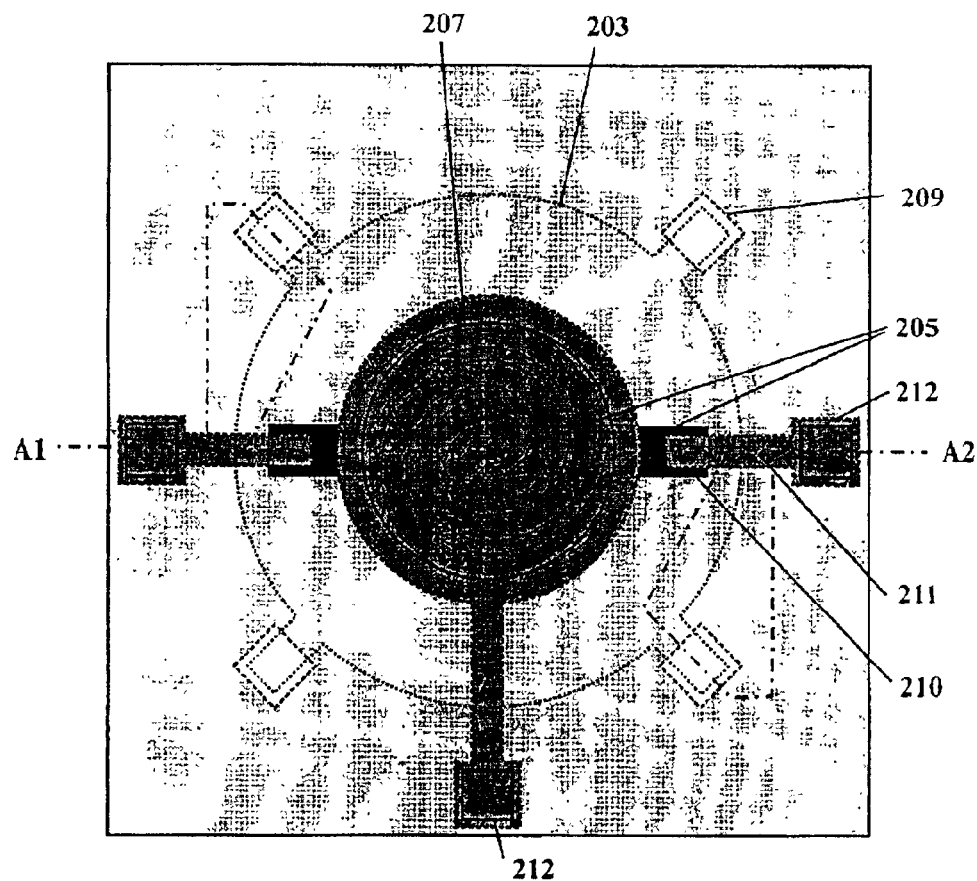
FIG. 2a is a plan view of a microelectrode having an electrode of smaller size than a sealed cavity.
Figure 2B:
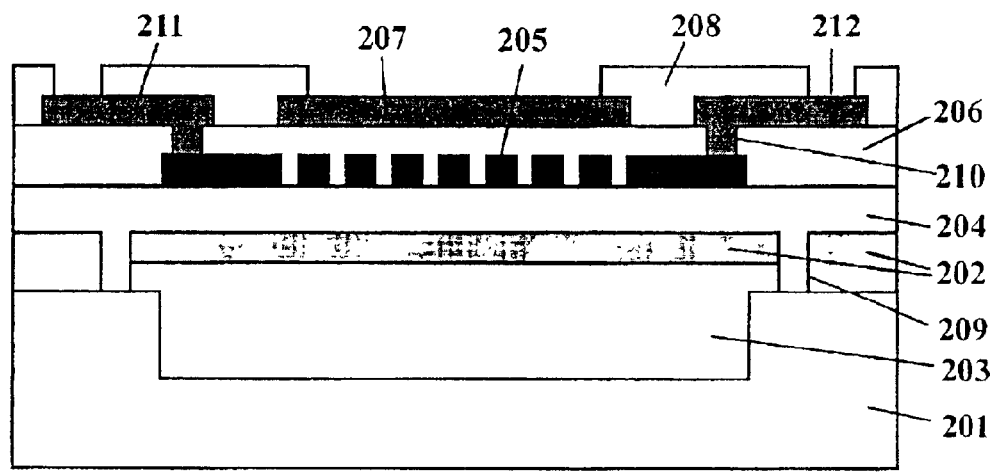
Figure 2C:
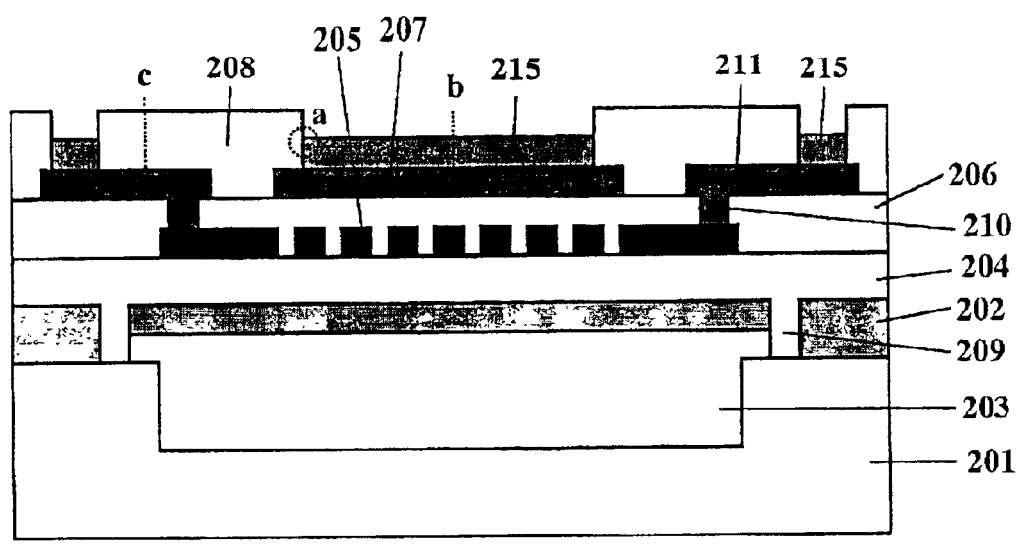
Figure 2D:
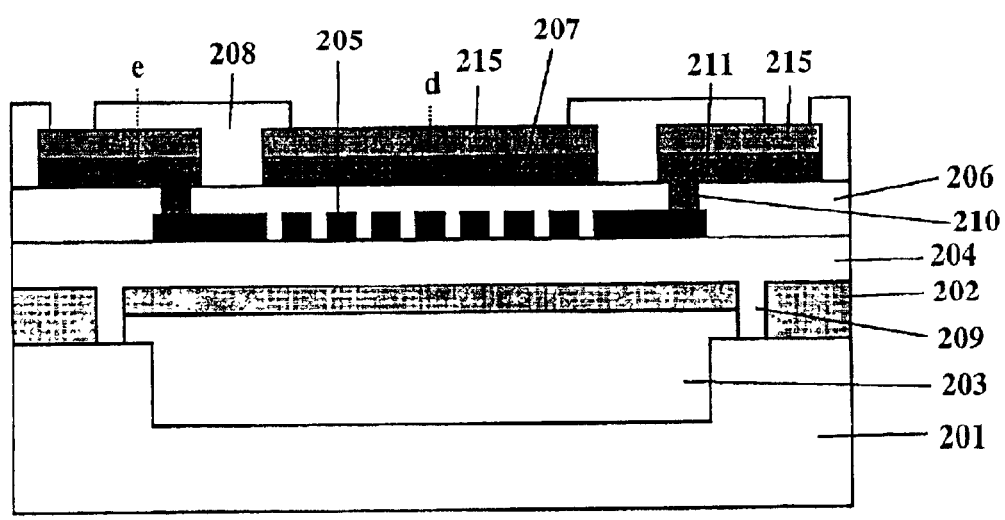
Figure 3A:
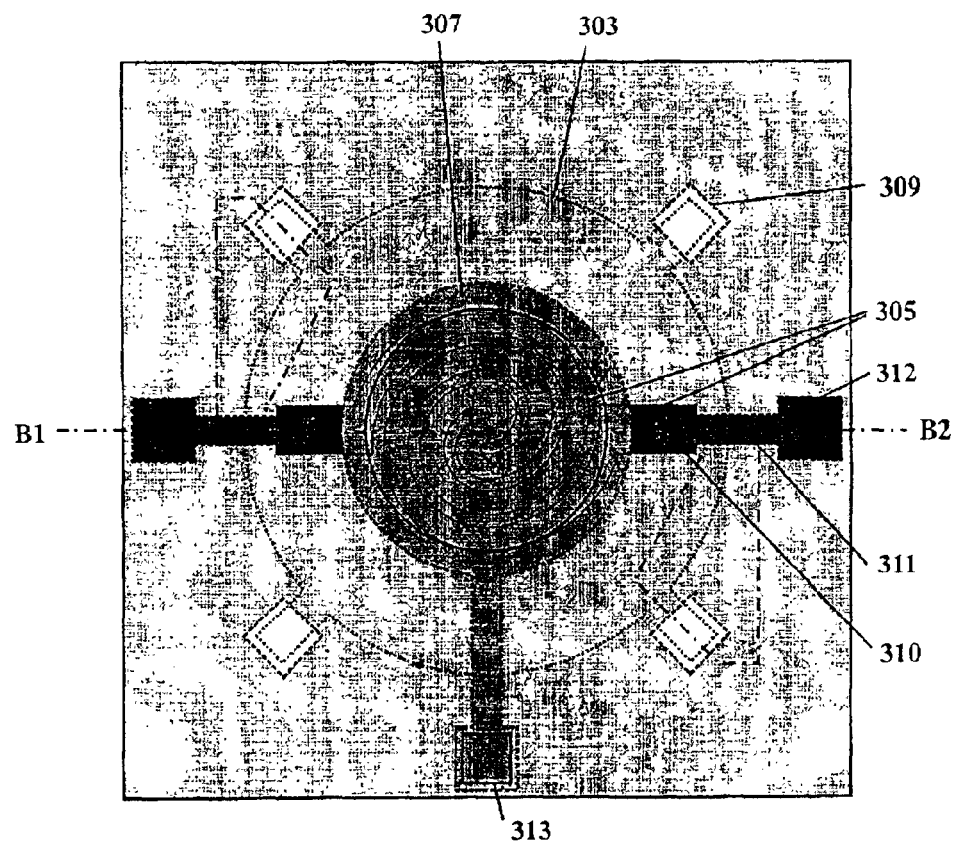
FIG. 3a is a plan view of a microelectrode of different kind than wirings and an electrode of a microheater.
Figure 3B:
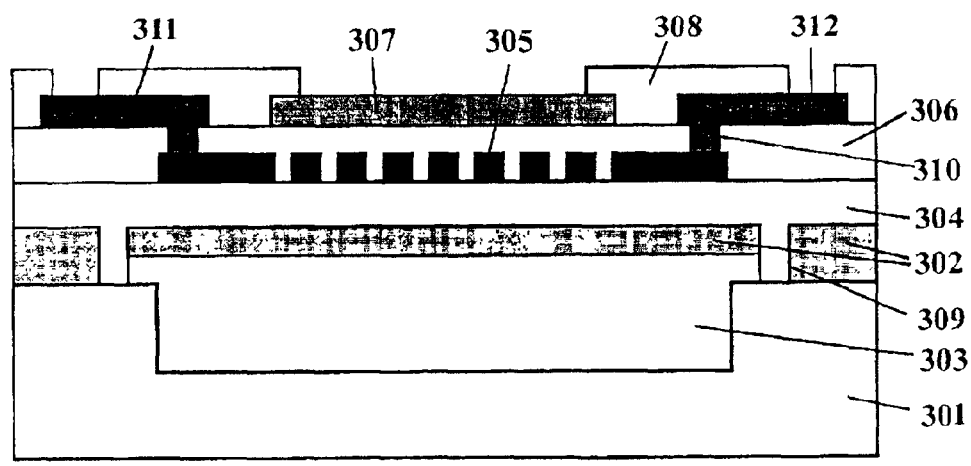
Figure 3C:
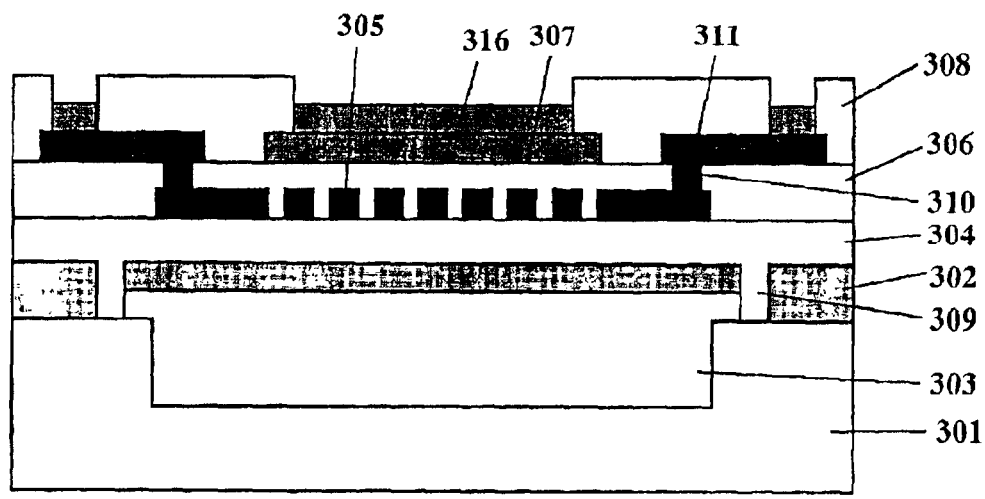
Figure 4A:
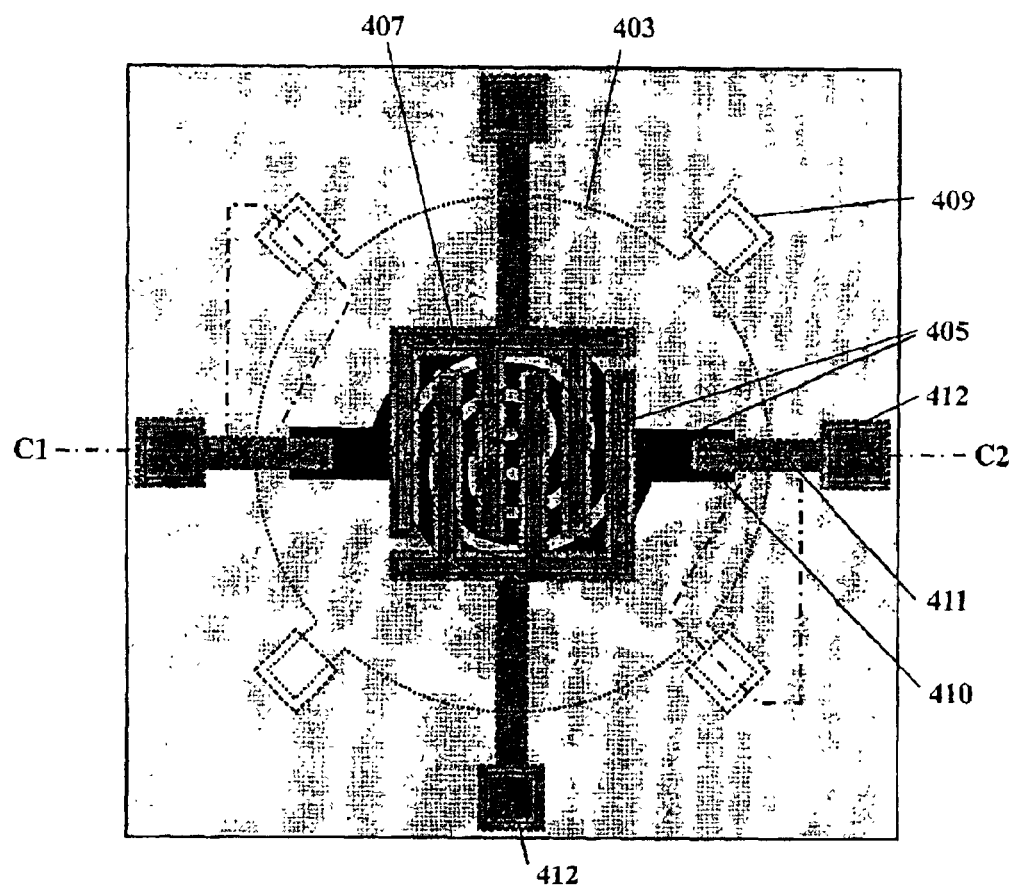
FIG. 4a is a plan view of microelectrode having electrode of an IDA structure.
Figure 4B:
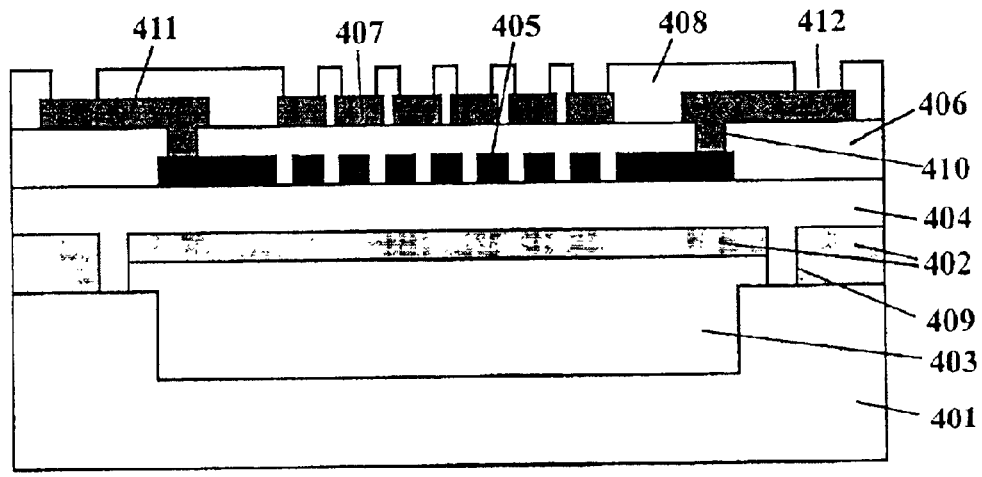

FIGS. 2a to 3c and FIGS. 5a to 7b show structures in which the electrodes is composed of one planar electrode, and FIGS. 4a and 4b are examples in which the electrode 407 is composed of IDA structure.

Also in FIGS. 2a to 3c and 5a to 7b, the electrodes 107, 207, 307, 407, 507, 607 and 707 can be composed of IDA structure. In FIGS. 2a to 2d, the wiring 211 and the electrode 207 are formed with same material, however, in FIGS. 3a to 3c, the wiring 311 and the electrode 307 are formed with different materials. Also in FIGS. 4a to 7b as in FIGS. 3a to 3c, the wirings 411, 511, 611 and 710 and the electrodes 407, 507, 607 and 707 are formed with different materials.

FIGS. 2b to 2d show sectional views taken along line A1–A2 of FIG. 2a, respectively.

FIGS. 3b to 3c show sectional views taken along line B1–B2 of FIG. 3a, respectively.

FIG. 4b shows a sectional view taken along line C1–C2.

Figure 5A:
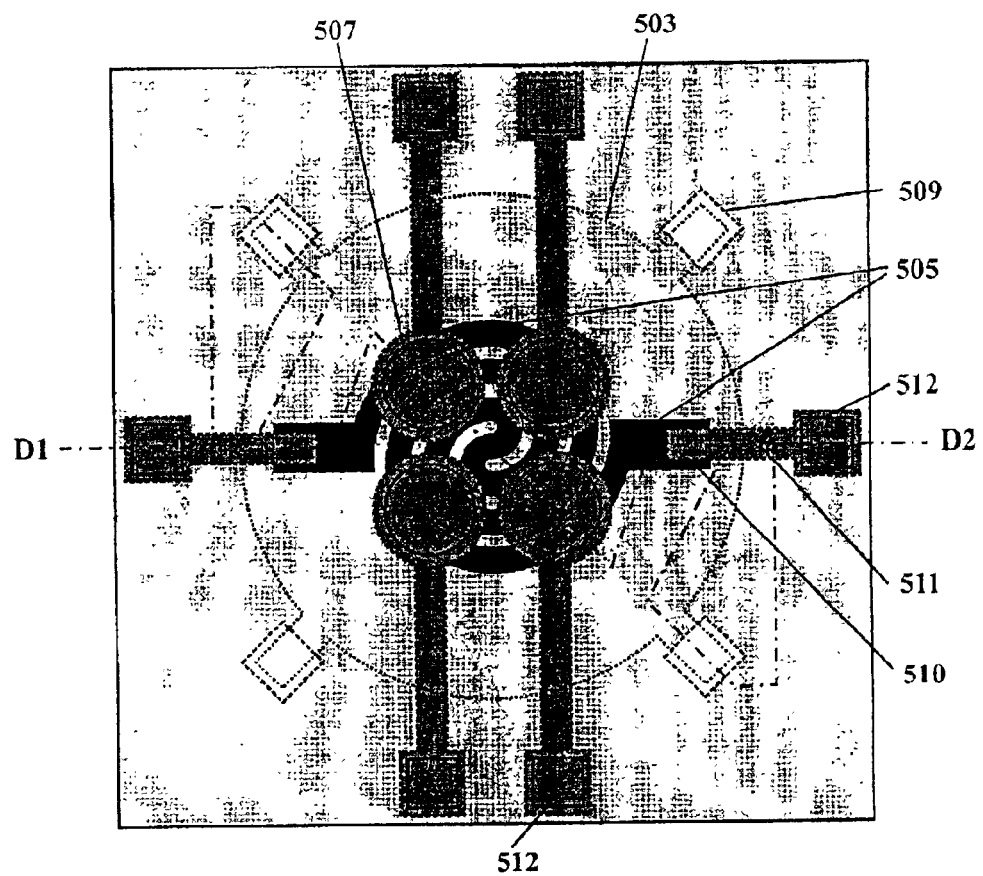
FIG. 5a is a plan view of a microelectrode having a plurality of electrodes on one sealed cavity.
Figure 5B:
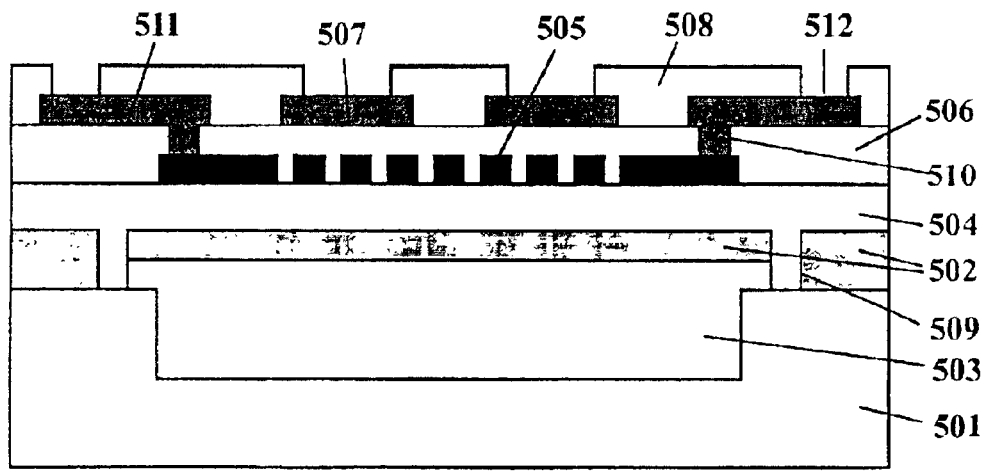

FIGS. 5a and 5b show a case where two or more electrodes exist on one sealed cavity 503. When heating a plurality of electrodes 507 with one microheater 505, the microelectrode having a structure of FIG. 5a can be used. FIG. 5b shows a sectional view taken along line D1–D2 of FIG. 5a.

Figure 6A:
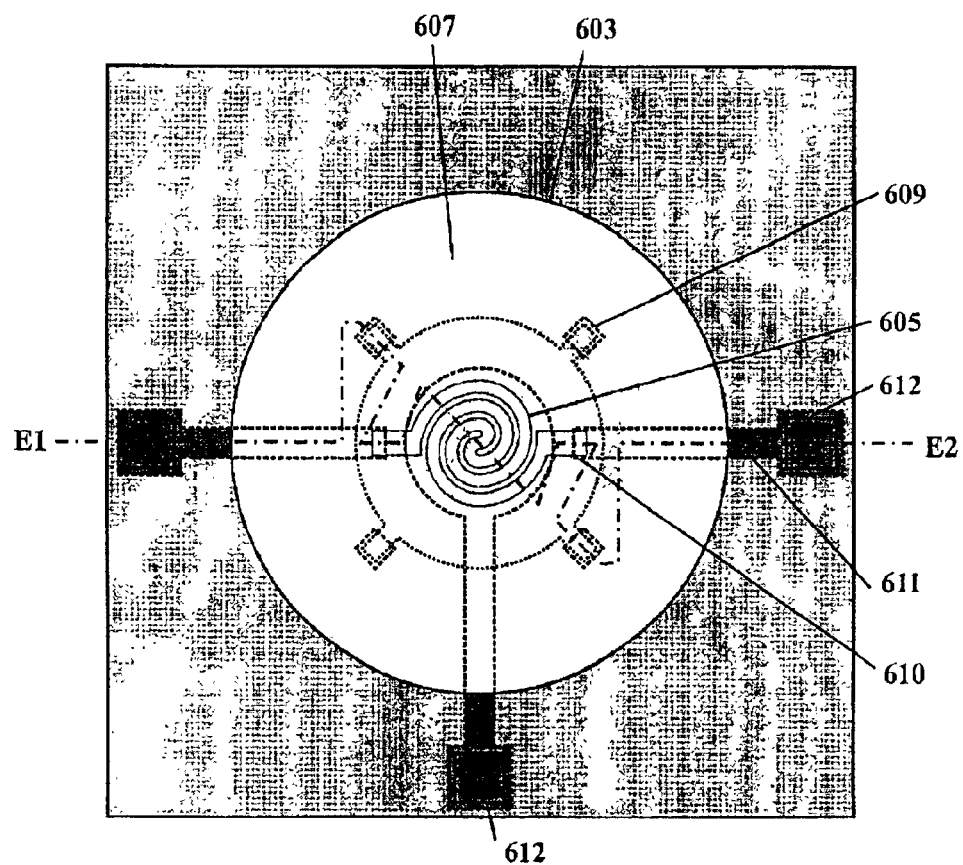
FIG. 6a is a plan view of microelectrode having a metal electrode of large size than a sealed cavity.
Figure 6B:
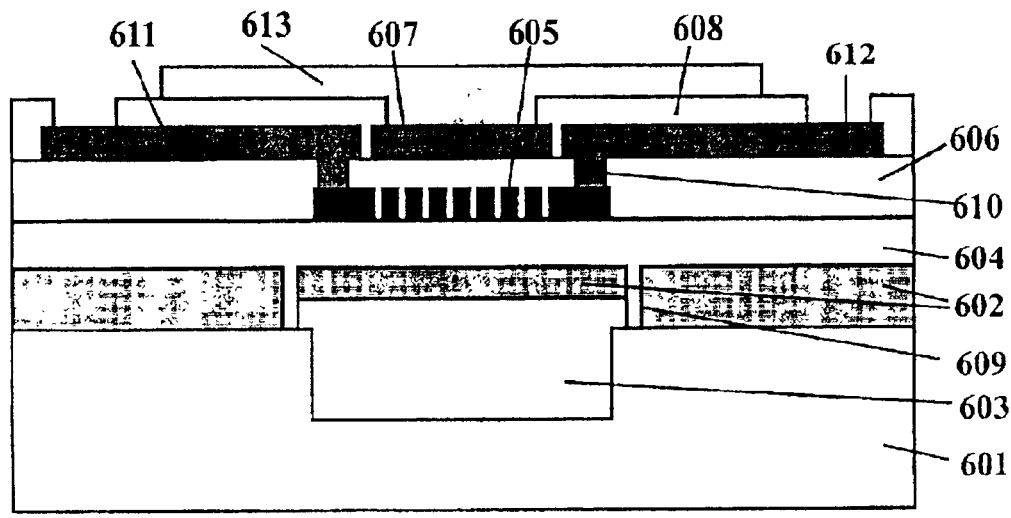
Figure 7A:
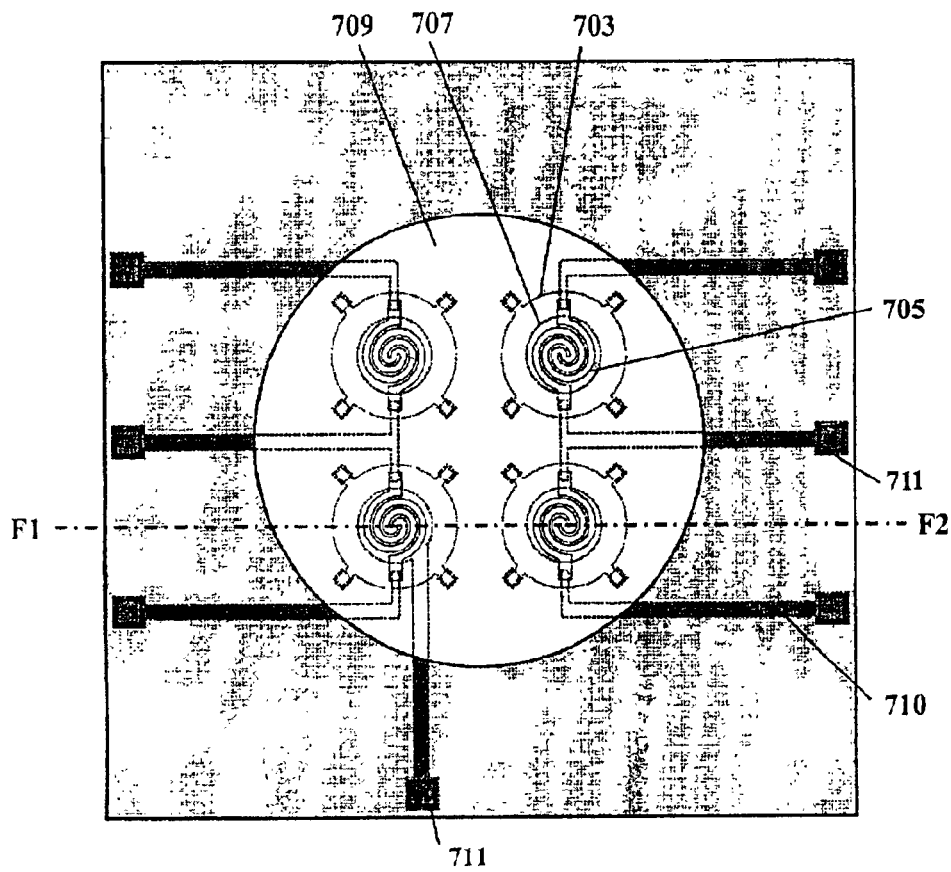
FIG. 7a is a plan view of a microelectrode having one metal electrode on a plurality of sealed cavities.
Figure 7B:
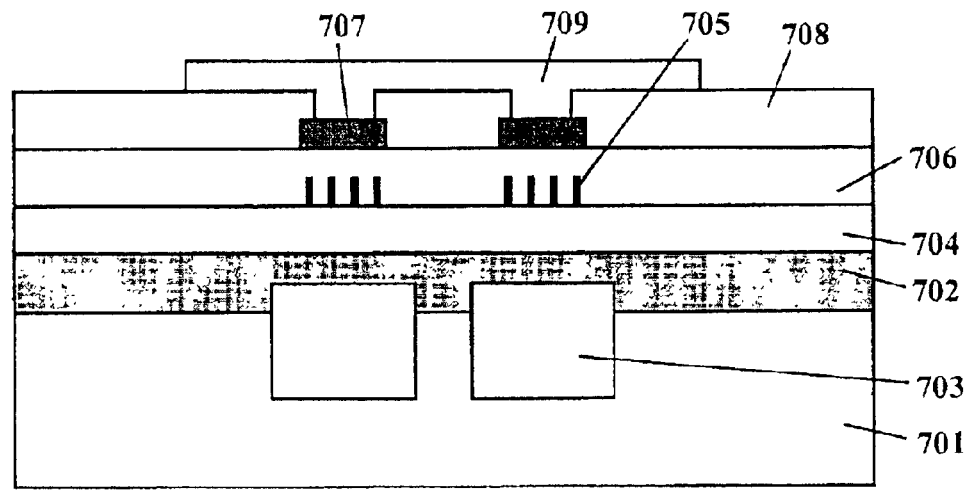

FIGS. 6a and 6b show a case where the sizes of microheater 605 and the sealed cavity 603 are smaller than the metal electrode 613. A microelectrode having a structure of FIG. 6a is used to review the change in surface of the metal electrode 613 or in solution when heating the metal electrode 613 locally. FIG. 6b FIGS. 7a and 7b show a case where the microheater 705 and the sealed cavity 703 are smaller than the metal electrode 709 and a plurality of microheaters 705 and the sealed cavity 703 exist. A microelectrode having a structure of FIG. 7a can be used to review the change in surface of the metal electrode 709 or in solution when heating the metal electrode 709 locally at various portions at different temperatures. FIG. 7b shows a sectional view taken along line F1–F2 of FIG. 7a.

Voltage is applied or current is flowed to the microheaters 105, 205, 305, 405, 505, 605 and 705 to heat the electrodes 107, 207, 307, 407, 507, 607 and 707, and at this time, the heat generated by Joule heating not only heat the upper electrodes 107, 207, 307, 407, 507, 607 and 707 but also heat the lower support films 102, 202, 302, 402, 502, 602 and 702, the sealed films 104, 204, 304, 404, 504, 604 and 704 and the silicon substrates 101, 201, 301, 401, 501, 601 and 701. The existence of the sealed cavities 103, 203, 303, 403, 503, 603 and 703 between the microheaters 105, 205, 305, 405, 505, 605 and 705 and the silicon substrates 101, 201, 301, 401, 501, 601 and 701 can substantially reduce heat loss to a lower part, so that applying even a small voltage or current to the microheaters 105, 205, 305, 405, 505, 605 and 705 can heat the electrodes 107, 207, 307, 407, 507, 607 and 707 at high temperature. Since thermal mass of the lower part is decreased, the electrodes 107, 207, 307, 407, 507, 607, 707 can be more rapidly heated or cooled. The larger the width of the sealed cavities 103, 203, 303, 403, 503, 603 and 703 or the deeper the depth of the sealed cavities 103, 203, 303, 403, 503, 603 and 703 in comparison with the size of the microheaters 105, 205, 305, 405, 505, 605 and 705, the heat loss is reduced. The present invention make it possible to form a deep cavity of about 1 to 100 μm by using a thermal oxidation sacrificial layer of a silicon trench array. Since the depth of a cavity is determined according to the depth of a trench, depth of the cavity can be made large by making large the depth of the trench by RIE (reactive ion etching) or deep RIE. Preferably, in case of making the inside of the sealed cavities 103, 203, 303, 403, 503, 603 and 703 to be vacuum, the heat isolation performance becomes better.

It is preferable that the support films 102, 202, 302, 402, 502, 602 and 702 existing on the sealed cavities 103, 203, 303, 403, 503, 603 and 703 is composed of a polysilicon film or a silicon nitride film. Sealing films 104, 204, 304, 404, 504, 604 and 704 existing between the microheaters 105, 205, 305, 405, 505, 605 and 705 and the support films 102, 202, 302, 402, 502, 602 and 702 not only act to seal the hole existing in the support films 102, 202, 302, 402, 502, 602 and 702 but also act to insulate the microheaters 105, 205, 305, 405, 505, 605 and 705 from the support films 102, 202, 302, 402, 502, 602 and 702. These sealing films 104, 204, 304, 404, 504, 604 and 704 are preferably composed of single layer or stacked layer of silicon oxidation film or silicon nitride film.

It is preferable to use platinum or doped polysilicon in making the microheater composed of resistors to make it possible that the microheater can be manufactured with CMOS process.

The electric insulation films 106, 206, 306, 406, 506, 606 and 706 is necessary to minimize the influence of current flowing through the microheaters 105, 205, 305, 405, 505, 605 and 705 on current flowing through the electrodes 107, 207, 307, 407, 507, 607 and 707. When the silicon oxide film and silicon nitride film are stacked to two layers or more, electric insulation becomes far better. Electrical insulation films 106, 206, 306, 406, 506, 606 and 706 are preferably composed of one or more layers of one or more elements selected from a silicon oxide film or a silicon nitride film, and more preferably composed of three layers of a LPCVD silicon oxide film, a LPCVD silicon nitride film and a LPCVD silicon oxide film.

In the solution, corrosion of the wirings 211, 311, 411, 511, 611 and 710 through pinhole of the protection films 208, 308, 408, 508, 608 and 708 becomes a problem. In case where the wirings 213 and 215 are composed of aluminum in structure of FIGS. 2c and 2d, aluminum is corroded through pinhole of protection film 208 in the direction of c and e, and corrosion becomes further severe if temperature rises. When silicon oxide films or silicon nitride films are stacked in two or more layers as protection film 208, corrosion of wirings 211, 311, 411, 511, 611 and 711 through pinhole is substantially decreased. To minimize corrosion of wirings 211, 311, 411, 511, 611 and 710, protection films 208, 308, 408, 508, 608 and 708 is preferably formed of one or more layers from one or more elements selected from a silicon oxide film or a silicon nitride film, and more preferably formed of three layers of a PECVD silicon oxide film, a PECVD silicon nitride film and a PECVD silicon oxide film.

Microheaters 205, 305, 405, 505, 605 and 705 are connected to wirings 211, 311, 411, 511, 611 and 710. In this case, total resistance is determined by resistance of microheaters 205, 305, 405, 505, 605 and 705 and resistance of wirings 211, 311, 411, 511, 611 and 710. To have constant resistance regardless of length of wirings 211, 311, 411, 511, 611 and 711, resistance of wirings 211, 311, 411, 511, 611 and 710 must be far smaller than that of the microheaters 205, 305, 405, 505, 605 and 705. Although it is possible to make resistance of wirings 211, 311, 411, 511, 611 and 710 relatively small by making resistance of the microheaters 205, 305, 405, 505, 605 and 705 large, however, if resistance of the microheaters 205, 305, 405, 505, 605 and 705 is large, then there is a problem that voltage applied must be high. Therefore, it is necessary to make resistance of the wirings 211, 311, 411, 511, 611 and 710 very small. With aluminum, it is possible to obtain a micropattern of small specific resistivity and with easy way. Therefore, it is preferable to form wirings 211, 311, 411, 511, 611 and 710 by using aluminum among platinum and aluminum which can be used in CMOS process. Corrosion of aluminum which becomes problem when using aluminum can be minimized by protection films 208, 308, 408, 508, 608 and 708 formed by stacking a silicon oxide film or a silicon nitride film in two or more layers as described above.

In case of using aluminum as wirings 211, 311, 411, 511, 611 and 710, a microelectrode of gold or platinum can be obtained by forming a metal electrode 214 with gold or platinum after simultaneously forming the electrode 213 and the wiring 215 as shown in FIG. 2c, or by forming the electrodes 217 and 219 and the wiring 218 and 220 in two layers of aluminum and platinum. However, corrosion of aluminum occurs through pinhole in a portion and in direction of b of FIG. 2c and pinhole in direction of d of FIG. 2d. Furthermore, in case of raising the temperature of the electrode, corrosion of aluminum through pinhole is increased rapidly. Therefore, it is preferable to minimize the corrosion of an electrode 307 by forming the electrode 307 with platinum including no aluminum and independently from the wiring 311 as shown in FIG. 3b.

Metal which can be used as electrodes 107, 207, 307, 407, 507, 607 and 707 in a standard CMOS process is limited to several metals such as platinum, aluminum, etc. Metals generally used in solution are precious metals (platinum, gold and iridium) which are resistant to corrosion, however, metals except platinum cannot be used in a standard CMOS process. Therefore, when making an electrode of gold, it is preferable to form a metal electrode composed of gold by performing lift-off process as a last process after making an electrode in a standard CMOS process.

Even if the electrodes 107, 207, 307, 407, 507, 607 and 707 made of platinum is formed, since protection films 108, 208, 308, 408, 508, 608 and 708 is laid on surface of platinum and etched therefrom in the process, foreign materials exist in the platinum surface. Since this foreign materials can substantially change the electrochemical performance of platinum, to obtain a surface of pure platinum, it is preferable to form a platinum metal electrode 316 by the lift-off method on the platinum electrode 314 as shown in FIG. 3c.

In the microelectrode array of the present invention having a basic structure of a microelectrode shown in FIG. 1a, two or more microelectrodes shown in FIG. 1a exist in a silicon substrate 101. In addition, in the microelectrode array of the present invention having structure of the microelectrode of FIGS. 2a to 7b, two or more microelectrodes of FIGS. 2a to 7b exist in silicon substrates 201, 301, 401, 501, 601 and 701.

FIGS. 8a to 9b are sectional views and plan views of a microelectrode array composed of four (4) microelectrodes shown in FIG. 2a. FIG. 8b shows a sectional view taken along line G1–G2 of FIG. 8a.

Figure 8A:
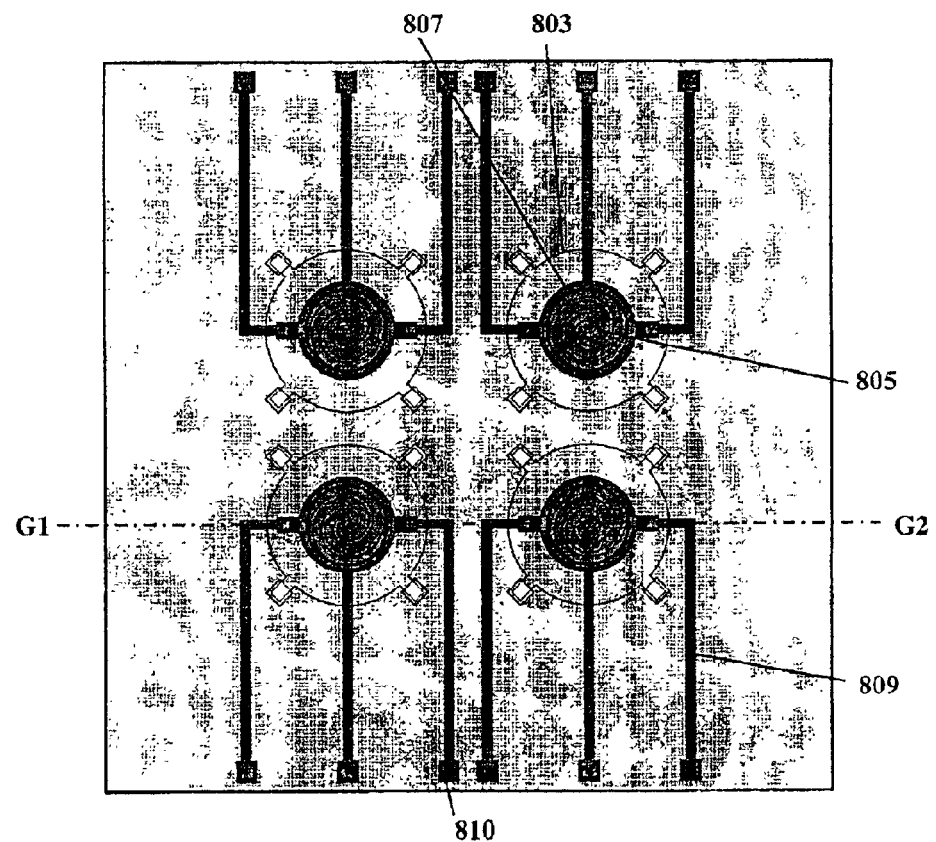
FIG. 8a is a plan view of microelectrode array according to the present invention having a structure in which two wirings of each microheater are connected to a pad respectively.
Figure 8B:
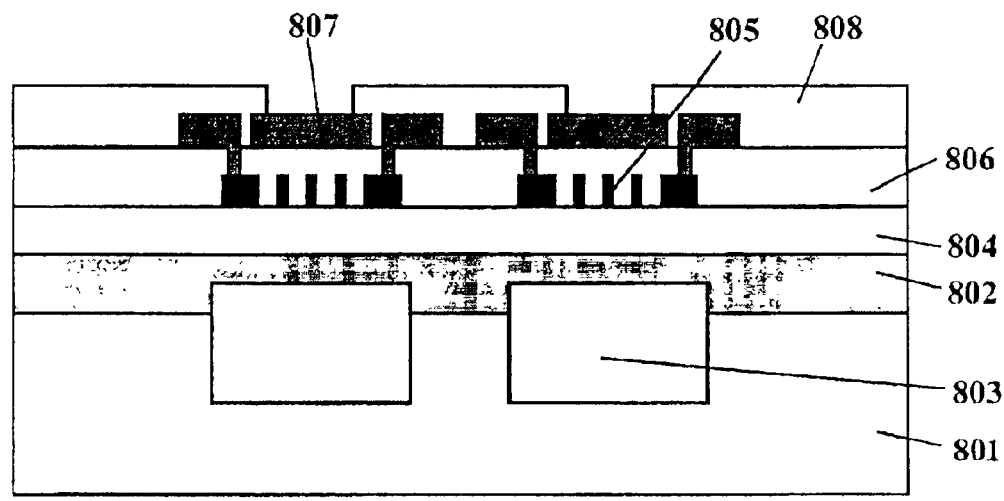
FIG. 8b is a sectional view to illustrate FIG. 8b.
Figure 9A:
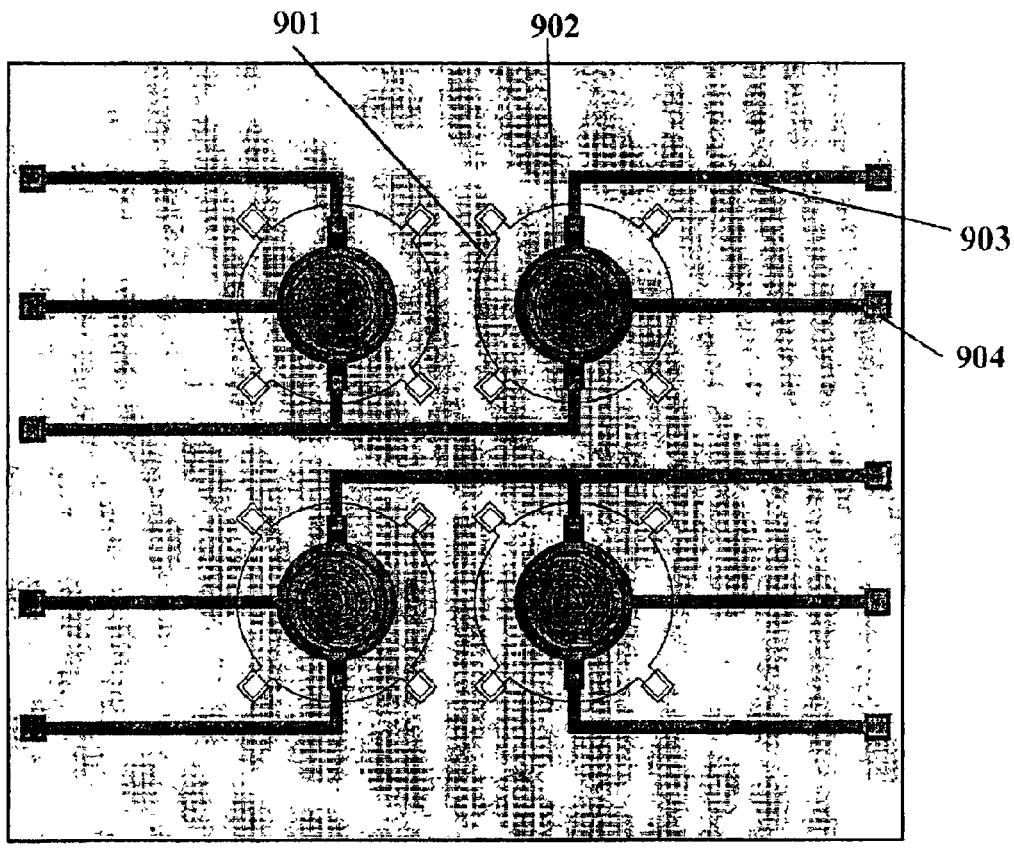
FIG. 9a is a plan view of a microelectrode array according to the present invention having a structure in which each wiring of a microheater is connected to one pad.
Figure 9B:
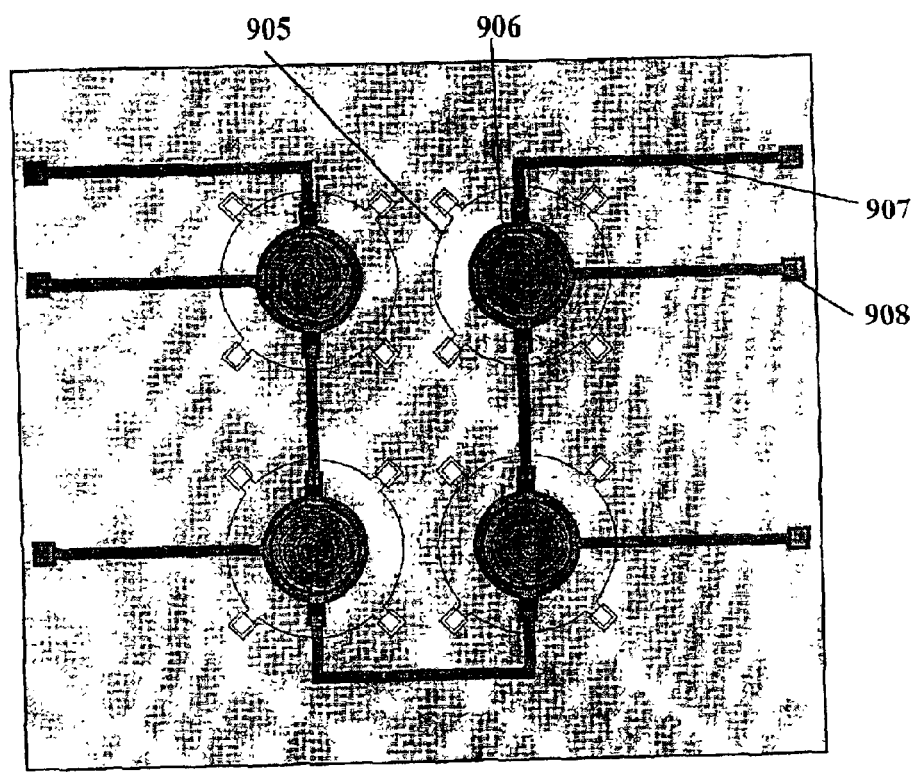
FIG. 9b is a plan view of a microelectrode array having a structure in which all wirings of a microheater are connected to two pads.

The structure shown in FIG. 8b comprises a silicon substrate 801, sealed capacities 803, 901 and 905, a support film 802, a sealing film 804, a micorheater 805, an electric insulation film 806, electrodes 807, 902 and 906, a protection film 808, wirings 809, 903 and 907, pads 810, 904 and 908. FIGS. 8a and 8b show a structure in which each of two wirings 809 of each microheater 805 is independently connected to a pad 810, FIG. 9a shows a structure in which one of two wirings 903 of each microheater among two or more microheaters is connected to one pad 904, FIG. 9b shows a structure in which a wiring 907 of all microheaters is connected to only two pads 908 among two or more microheaters. Since as the number of electrodes increases the number of wirings 809, 903 and 907 of microheaters increases, it is required to decrease the number of wirings 809 as much as possible. To reduce the number of wirings 809, it is preferable to manufacture a microelectrode array according to the structure of FIGS. 9a and 9b. Not only the microelectrode of FIG. 2a but also the microelectrode of FIGS. 3a to 7b can be presented to microelectrodes of the shape shown in FIGS. 8a to 9b. In addition, a microelectrode array in which the metal electrode 109 exists as shown in FIG. 1b can be presented in all cases.

FIGS. 10a to 10l are sectional views to illustrate the manufacturing process of a microelectrode shown in FIG. 3a among various types of microelectrodes and microelectrode arrays.

Entire process use eight(8) pattern masks, and a silicon wafer is used as a substrate. The process is proceeded to the steps of forming a thermal oxidation prevention film 1002, forming a silicon trench array 1005 on the surface of a silicon substrate 1001, forming a sacrificial layer 1006 by thermally oxidizing the silicon trench array 1005, removing the thermal oxidation prevention film 1002, forming a sacrificial layer 1009 with silicon oxide film on the silicon substrate 1001 and the sacrificial layer 1006 to form an etching path, depositing a polysilicon support film 1010 on the entire surface of a sacrificial layer and forming an etching hole 1011, forming a cavity 1012 by removing the two sacrificial layers through the etching hole 1011, sealing the cavity 1012 by depositing a sealing film 1013 on the etching hole 1011, forming a microheater 1015, forming an electric insulation film 1017, forming a contact hole 1016 for connecting the microheater to wiring, forming a wiring 1018, an electrode 1019, and a pad 1021, forming a protection layer 1020 on the electrode 1019, the pad 1021, the wiring 1018 and an insulation film 1017, exposing a portion of the electrode 1019 and pad 1021 by etching a portion of the protection film 1020, and forming a metal electrode 1022 on the electrode 1019.

Figure 10A:
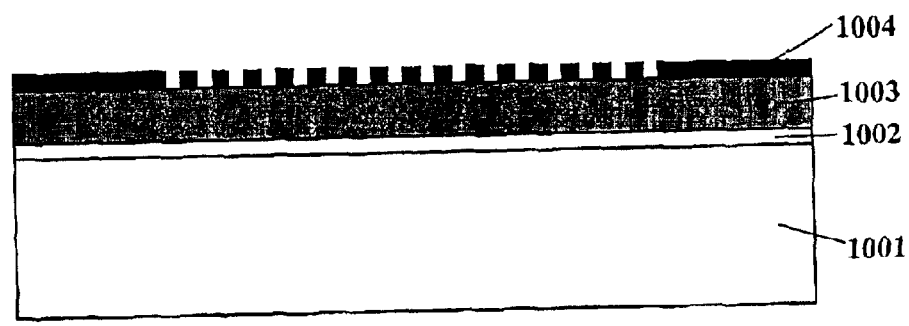
FIGS. 10a to 10l are sectional views to illustrate the process of manufacturing a microelectrode according to the present invention.

Referring to FIG. 10a, a silicon nitride film 1002 and a silicon oxide film 1003 are sequentially formed on the silicon substrate 1001, thereafter, photoresist 1004 is coated on the silicon oxide film 1003, then exposing to light by using a first mask, then patterning, thereby defining portions for forming a plurality of silicon trench arrays. A p-type 5 inch silicon substrate 1001 having crystal direction of <100> is used as a basic substrate via a standard cleaning process. A silicon oxide film 1003 acts to prevent the etching of the silicon nitride film 1002 which is used as a thermal oxidation prevention film, and is grown by LPCVD or PECVD.

Figure 10B:
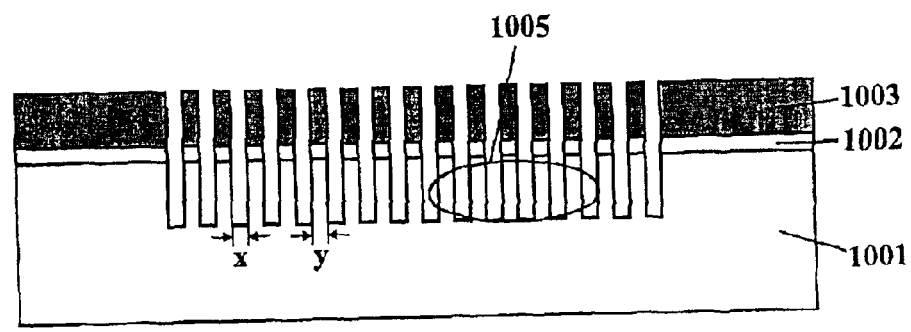

Referring to FIG. 10b, a silicon oxide film 1003 and a silicon nitride film 1002 of exposed portion are sequentially dry etched, thereafter, photoresist 1004 is removed. Silicon trench array 1005 structure is formed by dry etching to the depth of 1 to 100 μm the exposed silicon substrate 1001 exposed with reaction ion etching or deep RIE. Then, $POCl_3$ is diffused for 30 minutes in a furnace at 900C, whereby the silicon substrate 1001 is doped with $n^+$. At this time, the ratio of size of x:y of trench line breadth is made to be 0.45:>0.55 so that micro porosity 1007 is formed between trench thermal oxide films 1006 which are generated by silicon thermal oxidation (refer to FIG. 10c). In addition, the thermal oxidation rate of silicon trench array is further increased by doping of the silicon substrate 1001 (refer to FIG. 10c), which makes the trench thermal oxide film 1006 including P to be easily removed by HF etching (refer to FIG. 10f).

Figure 10C:
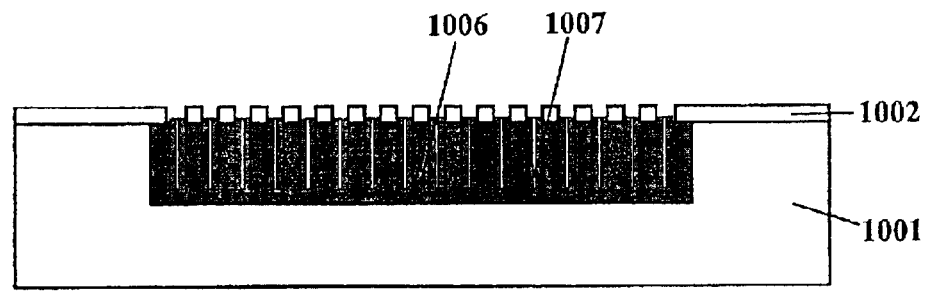

Referring to FIG. 10c, the silicon oxide film 1003 and etch residue are removed by wet etching in 6:1 BHF solution. The thermal oxidation process is proceeded using the silicon nitride film 1002 as an oxide mask in a furnace of the atmosphere of $O_2$ or $H_2/O_2$ and 900 to 1000° C. so as to form a trench thermal oxide sacrificial layer 1006 including P in a micro silicon trench array 1005, so that an area is defined in which sealed cavity 1014 having one side size or diameter of 1 to 1000 μm is to be formed. At this time, a plurality of micro porosity 1007 having depth of 0.1 to 0.3 µm are formed at the same time in the trench thermal oxide sacrificial layer 1006. The micro porosity 1007 acts as micro capillary which makes wet etching solution or vapor etching gas to penetrate well at the time of removing the trench thermal oxide sacrificial layer 1006.

Figure 10D:
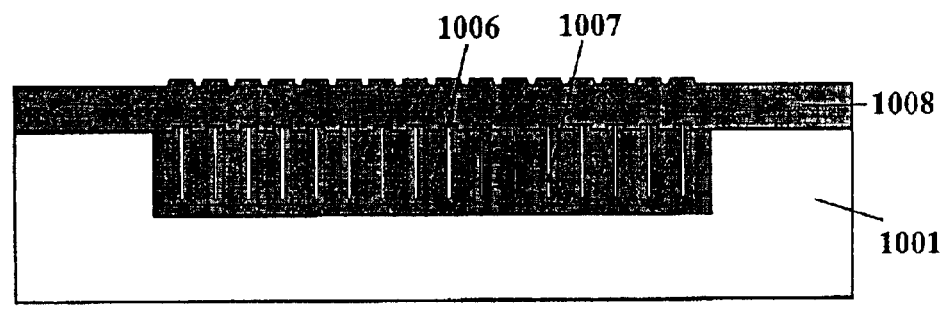

Referring to FIG. 10d, the silicon nitride film 1002 is removed by $H_3PO_4$ solution, and then, low temperature silicon oxide film $SiO_2$ 1008 of the thickness of 0.1 to 2 µm is deposited by LPCVD.

Figure 10E:
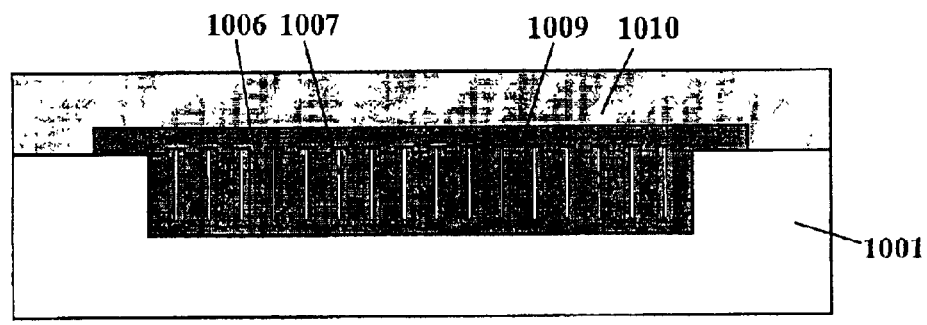

Referring to FIG. 10e, to define a sacrificial layer 1009 area to be used as an etching path, a low temperature silicon oxide film 1008 is doped with photoresist, exposed by using a second mask, thereafter patterning, so as to define an etching path portion. A low temperature silicon oxide film 1008 is wet etched in 6:1 BHF solution so that a low temperature silicon oxide sacrificial layer 1009 is formed which is branched to outside in the edge of the silicon trench sacrificial layer 1006 area. Prior to performing this process, it is preferable to polish and planarize the surface of the low temperature silicon oxide film 1008 to thickness of 0.1 to 1.0 µm by chemical mechanical polishing technique to reduce the roughness of surface. After removing the photoresist, cleaning is done, and a polysilicon support film 1010 is formed by depositing polysilicon to the thickness of 0.4 to 2.0 µm on entire upper surface with LPCVD. Compression pressure applied to the polysilicon support film 1010 is reduced by postannealing for two hours in furnace of atmosphere of 1000° C. and $N_2$.

Figure 10F:
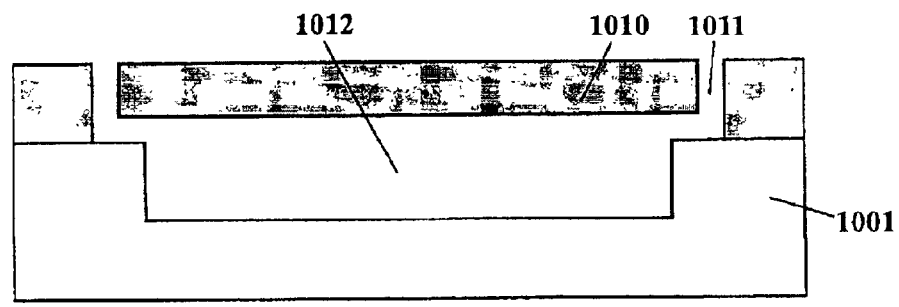

Referring to FIG. 10f, to form etching hole 1011 for introducing wet etch solution or vapor etch gas at the time of removing the trench thermal oxide sacrificial layer 1006 and a low temperature silicon oxide sacrificial layer 1009, photoresist is doped and exposed by using third mask and patterned to define an etch hole 1011 portion. A plurality of etch hole 1011 is formed by dry etching polysilicon support film 1010. The trench thermal oxide sacrificial layer 1006 and the low temperature silicon oxide sacrificial layer 1009 are removed by performing wet etching or vapor etching after removing the photoresist. In case of micro structure having 4 etching holes 1011 of diameter of 200 µm and depth of 5 µm, the structure is dipped in concentrated hydrofluoric acid solution for 30 minutes to 10 hours so as to rapid etch the trench thermal oxide sacrificial layer 1006 and the low silicon oxide sacrificial layer 1009 including P in an area where cavity is to be formed, and thereafter etch residue is removed which can be generated at the time of etch reaction by dipping it in 2:1 BHF solution. At this time, etch solution penetrate up to bottom of the trench thermal oxide sacrificial layer 1006 with ease by capillary force due to micro porosity 1007 formed between the trench thermal oxide sacrificial layer 1006. On the other hand, silicon wafer is introduced in gas phase etching equipment at the time of vapor etching, and substrate temperature is adjusted to 22 to 35° C., and pressure of reaction furnace is adjusted to 10 to 100 Torr, then thereafter, the trench thermal oxide sacrificial layer 1006 and the low silicon oxide sacrificial layer 1009 are removed by HF etching reaction in vapor state by flowing anhydrous HF and $CH_3OH$ process gas. Further better etch result can be obtained if two methods of vapor etch and wet etch are combined for etching of the silicon oxide sacrificial layer 1009. Etch time can be reduced by widening the width of micro porosity 1007, or increasing the size of the etch hole 1011, or increasing the number of the etch holes 1011. Air cavity 1012 in which the polysilicon support film 1010 exists in the upper part is formed by removing the trench thermal oxide sacrificial layer 1006 and the low silicon oxide sacrificial layer 1009.

Figure 10G:
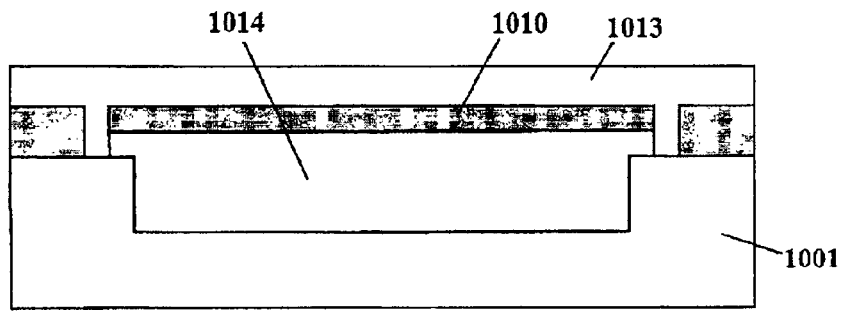

Referring to FIG. 10g, the thickness is reduced to 0.2 to 1.0 µm by heating for more than 30 minutes in vacuum furnace at 450° C. or in electric furnace of $N_2$ atmosphere, removing the water remained in surface, thereafter dry etching the polysilicon support film 1010. A sealing film 1013 composed of insulator such as a silicon oxide film or a silicon nitride film is deposited to single layer or stacked layers and to 4000 to 40000 Å by LPCVD or PECVD. At this time, since deposition process of the sealing film 1013 is performed in vacuum atmosphere, air in air cavity 1012 is discharged and the etch hole 1011 is sealed and a vacuum sealed cavity 1014 is formed.

Figure 10H:
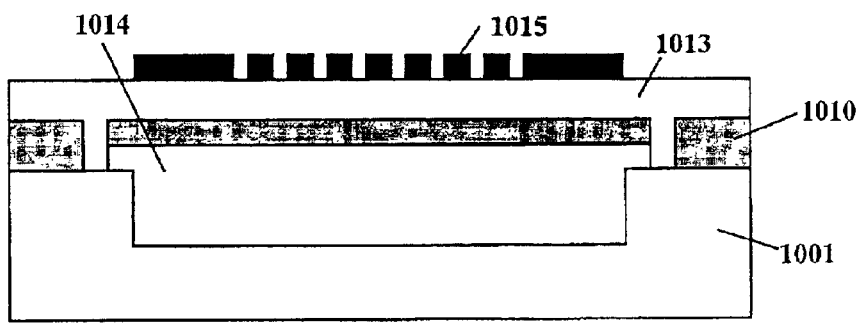

Referring to FIG. 10h, the polysilicon film 1015 of thickness of 0.2 to 0.6 µm is deposited by LPCVD, and then, to reduce the resistance of the polysilicon film 1015, the polysilicon film becomes an to $n^+$ type by diffusing $POCl_3$ for 30 minutes in electric furnace at 850 to 900° C. Etching portion is defined by coating photoresist film, exposing to light with a fourth mask, and patterning. The polysilicon film 1015 is dry etched to form a microheater 1015 composed of single body, and then photoresist film is removed.

Figure 10I:
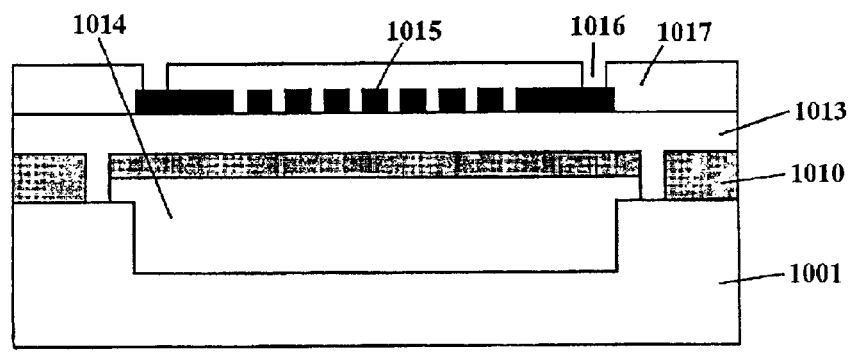

Referring to FIG. 10i, an electric insulation film 1017 composed of insulators such as a silicon oxide film or a silicon nitride film is deposited to single layer or stacked layers and thickness of 4000 to 40000 Å by LPCVD or PECVD. To maximize insulation performance, the insulation film 1017 is formed with three layers of an LPCVD silicon oxide film, an LPCVD silicon nitride film and an LPCVD silicon oxide film. Contact hole 1016 portion for contact of the microheater and the wiring is defined by coating photoresist film, exposing to light with a fifth mask, and patterning. Insulation film 1017 is dry etched or wet etched to form contact hole 1016 and then the photoresist film is removed.

Figure 10J:
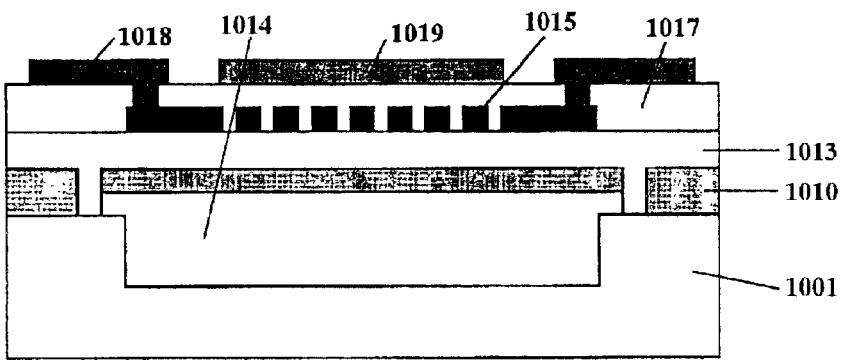

Referring to FIG. 10j, TiW of thickness of 750 to 2500 Å and Al of thickness of 8000 to 15000 Å are sequentially deposited by sputter technique. Wiring portion 1018 is defined by coating a photoresist film, exposing to light with a sixth mask, and patterning. TiW/Al is dry etched to form wiring 1018 and then the photoresist film is removed. TiW of thickness of 300 to 2500 Å and Pt of thickness of 1000 to 5000 Å are sequentially deposited by sputter technique. Electrode portion 1019 is defined by coating a photoresist film, exposing to light with a seventh mask, and patterning. At this time, wiring 1018 is again defined. TiW/Pt is dry etched or wet etched to form electrode 1019 and then the photoresist film is removed.

Figure 10K:
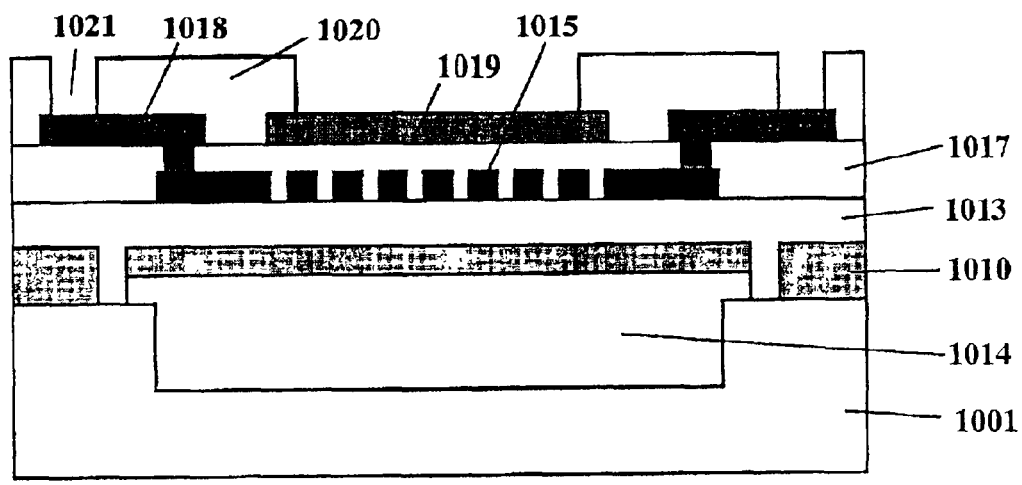

Referring to FIG. 10k, a protection film 1020 composed of insulators such as a silicon oxide film or a silicon nitride film is deposited to single layer or stacked layers and thickness of 0.5 to 5 µm by PECVD. At this time, to minimize corrosion of Al wiring 1018, the protection film 1020 is preferably formed with three layers of a PECVD silicon oxide film, a PECVD silicon nitride film and a PECVD silicon oxide film. Exposed portion of the electrode 1019 and a pad 1021 portion are defined by coating a photoresist film, exposing to light with an eighth mask, and patterning. Protection film 1020 is dry etched or wet etched to expose the electrode 1019 and the pad 1021 and then the photoresist film is removed.

Figure 10L:
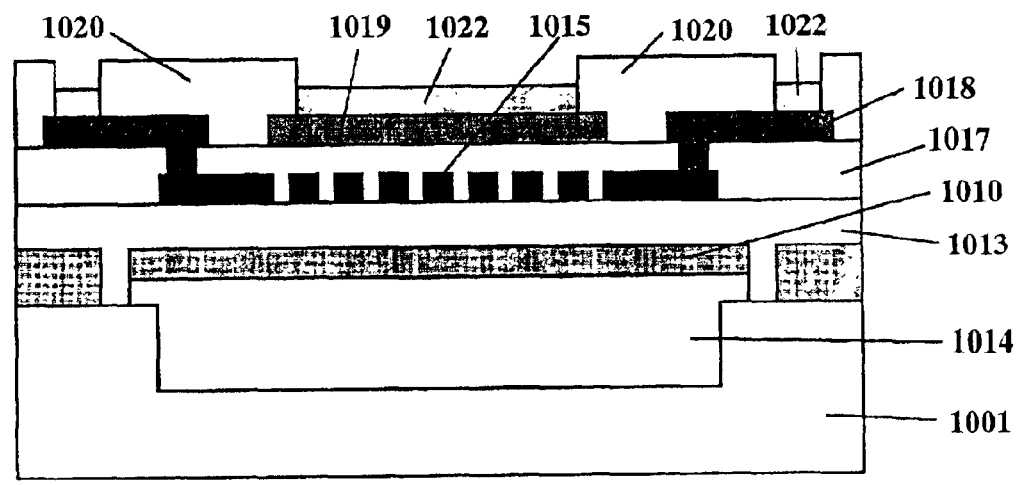

Referring to FIG. 10l, a metal electrode 1022 portion is defined by coating a photoresist film, exposing to light by an eighth mask, and patterning. Au is deposited to thickness of 1000 to 3000 Å on exposed electrode 1019 and wiring 1018 by e-beam technique under the condition that the photoresist film is remaining. Photoresist film is removed by dipping into acetone so as to leave only the metal electrode 1022 composed of Au on electrode 1019 and wiring 1018.

Figure 11:
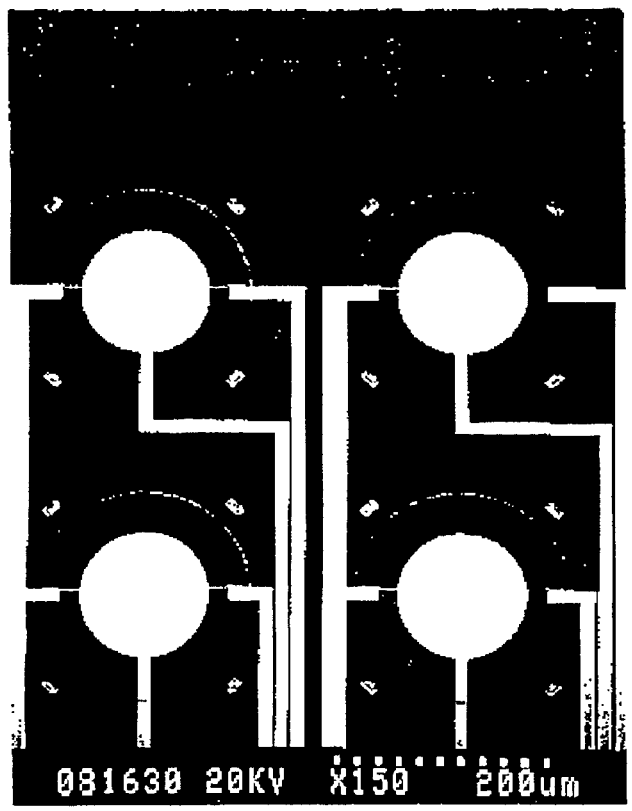
FIG. 11 is a SEM photograph taken of plan view of a microelectrode array having the structure of FIGS. 3a and 3b.

FIG. 11 is a SEM photograph taken of a plan after manufacturing the microelectrode array of structure shown in FIGS. 3a and 3b having circular sealed cavity having diameter of about 200 μm and circular electrode having diameter of about 120 μm by the process described above.

In the process described above, chemical/mechanical polishing and formation of metal electrode are omitted. Microelectrode array is shown composed of 4 microelectrodes where the exposed circular electrode has diameter of 100 μm and each microelectrode has 4 etching holes.

Figure 12:
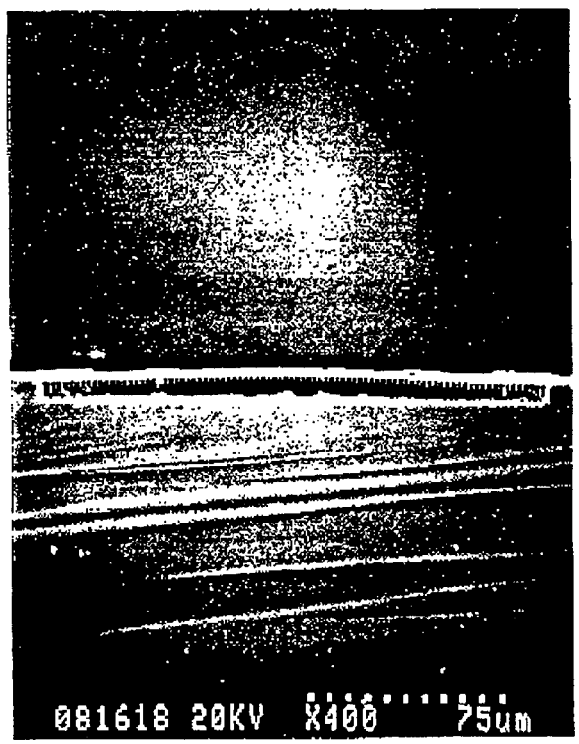
FIG. 12 is a SEM photograph taken of sectional view of a microelectrode array having the structure of FIGS. 3a and 3b.

FIG. 12 is a SEM photograph taken of section of microelectrode of FIG. 11, and shows that sealed cavity having depth of 5 μm is satisfactorily formed in uniform thickness in the bottom portion of silicon substrate.

Figure 13A:
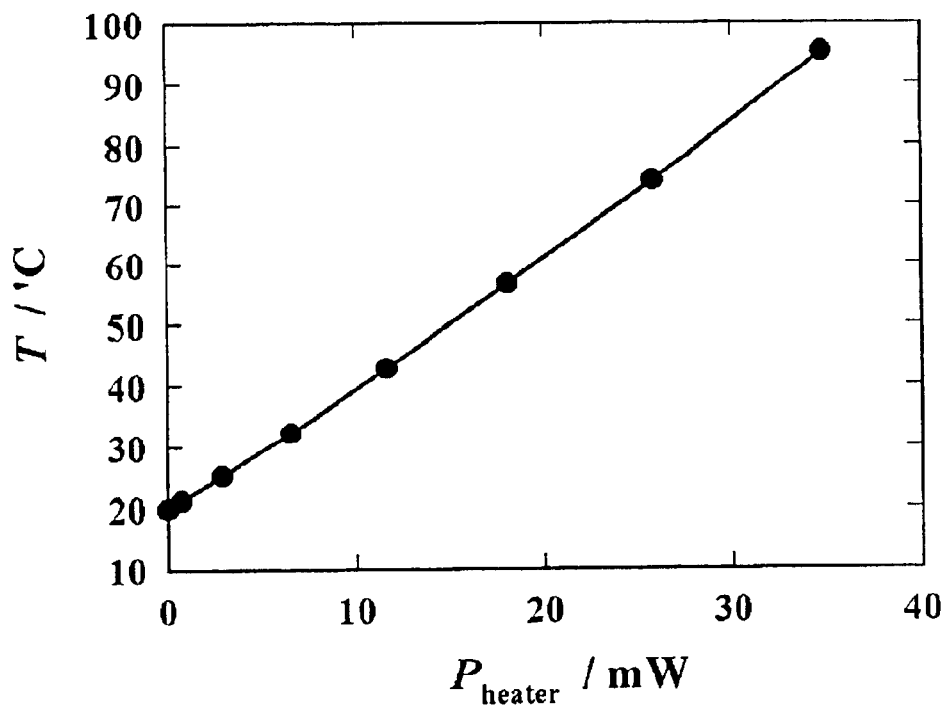
FIG. 13a is a graph showing the change of temperature of an electrode according to the electric power of a microheater having a sealed cavity.
Figure 13B:
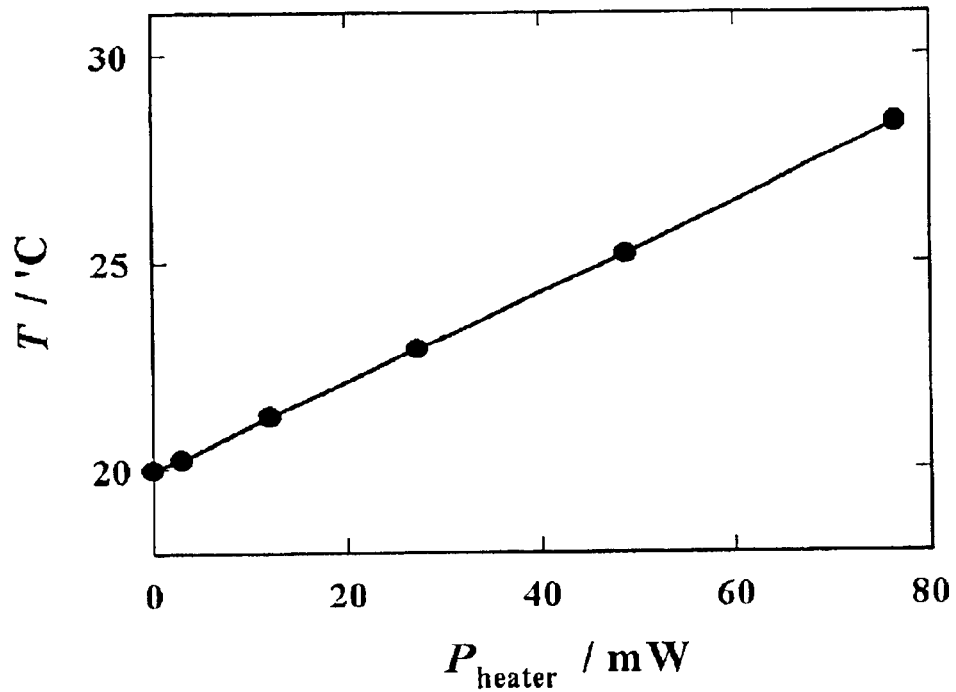
FIG. 13b is a graph showing the change of temperature of an electrode according to the electric power applied to a microheater in case of a microelectrode having no sealed cavity.

FIGS. 13a and 13b shows a change in temperature of electrode according to electric power of microheater when heating the microelectrode, manufactured with process described above, in 0.5 M $KNO_3$ solution. FIG. 13a is result when there is sealed cavity, and FIG. 13b is result when there is no sealed cavity. Heating performance is about 2.2° C./mW in case the sealed cavity exists, and heating performance is 0.11° C./mW in case the sealed cavity does not exist. It can be seen that the heating performance becomes about 20 times better due to existence of sealed cavity. In addition, in case there is sealed cavity, heating can be done up to 100° C. with ease with small electric power, however, in case there is no sealed cavity, it is difficult to maintain heated state at 20° C. or higher for long time due to limit of electric power which can be applied to microheater.

Figure 14:
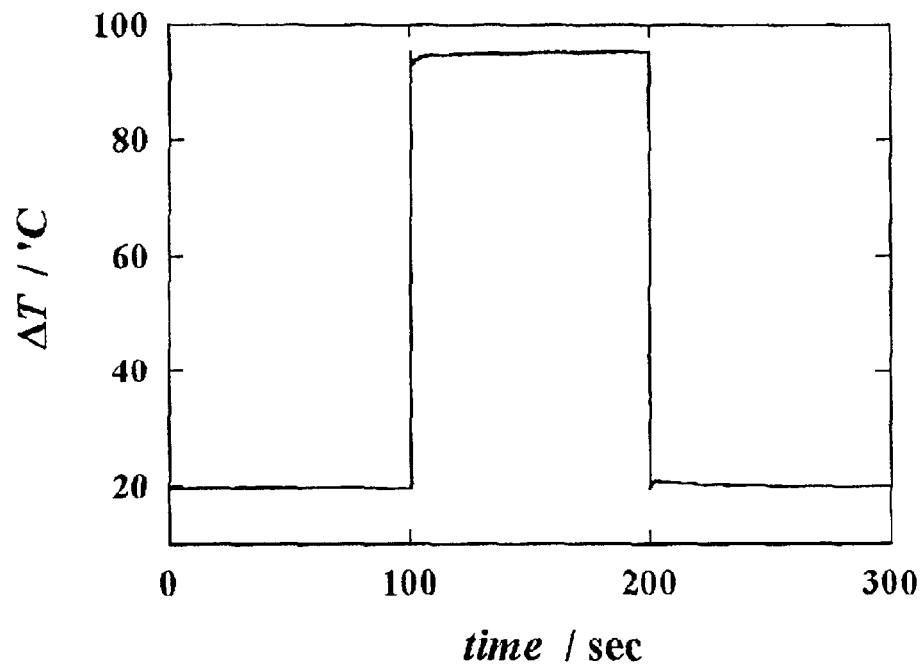
FIG. 14 is a graph showing the change of temperature of a microelectrode with the heating and cooling time.

FIG. 14 shows the change of temperature when heating in 0.5 $KNO_3$ solution from 20° C. to 95° C. and then cooling from 95° C. to 20° C. It can be seen that the level between 105% and 95% is reached within 0.2 second both at heating and cooling. That is, It can be seen that rapid heating and cooling can be accomplished by reducing the thermal mass around microheater due to use of sealed cavity.

Figure 15:
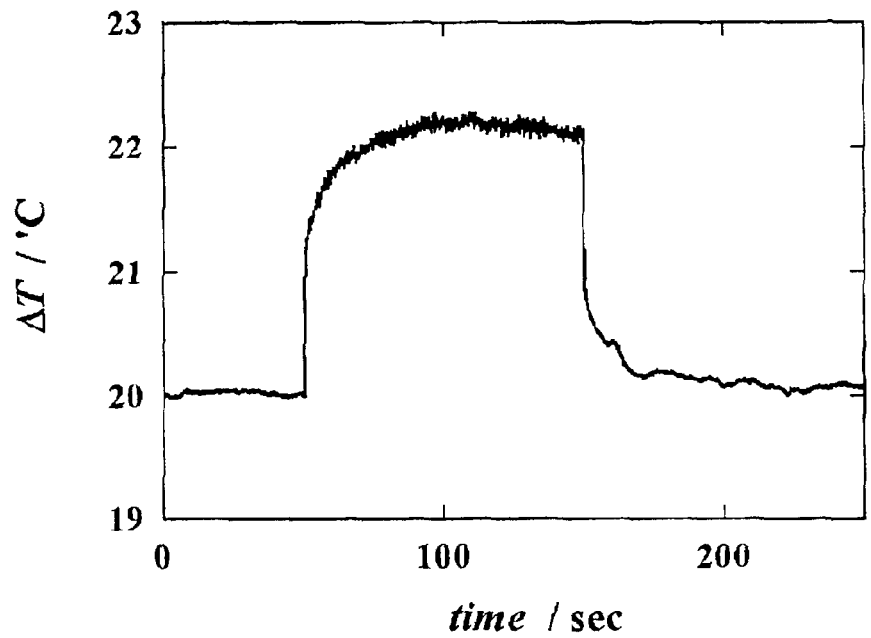
FIG. 15 is a graph showing the change of temperature of adjacent microelectrodes at the time of heating and cooling.

FIG. 15 shows the change of temperature of adjacent microelectrodes when heating and cooling one microelectrode in structure of FIG. 11. It can be seen that in case of heating the microelectrode from 20° C. to 95° C. in 0.5 $KNO_3$ solution and then cooling from 95° C. to 20° C., the temperature of microelectrode changes within 23° C. at the time of heating and comes back to original temperature at the time of cooling. That is, it can be seen that although two electrodes are apart no more than 300 μm, even when one electrode is heated, temperature of adjacent electrode is not substantially influenced. Therefore, in case forming microelectrode array by using microelectrode having structure described above, temperature of each electrode can be independently adjusted without substantially influencing the temperature of adjacent electrode.

It is confirmed that even when the microelectrode array shown in FIG. 11 is kept in 3 M KCl solution at room temperature for 10 days, corrosion does not occur. Therefore, it is seen that microelectrode having structure described above shows strong corrosion resistance performance in electrolyte solution.

According to the present invention described above, the microelectrode and the microelectrode array which have excellent thermal isolation between a microheater and a substrate, which has a small power consumption in solution, which has high heating and cooling speed can be manufactured by forming sealed cavity on silicon substrate.

In addition, microelectrode and microelectrode array which has good electric insulation between microheater and electrode, which can be used for long period without corrosion, and which is not influenced in its temperature performance by length of wiring can be manufactured.

Electrode and electrode array of the present invention not only be used as electrode for al electric/chemical measurement, but also can be applied to chemical sensor, biosensor, DNA chip, protein chip, electronic tongue and microreactor, etc. which use electro/chemical measurement technique.

Since those having ordinary knowledge and skill in the art of the present invention will recognize additional modifications and applications within the scope thereof, the present invention is not limited to the embodiments and drawings described above.

What is claimed is:

1. A microelectrode comprising:

a substrate having a trench;

a support film formed on said substrate so that a cavity is formed in said trench;

a sealing film formed on said support film to seal said cavity;

a microheater formed on said sealing film, with said microheater being composed of resistor which can diffuse heat;

an insulation film formed on said sealing film and said microheater;

a plurality of wirings formed on portions of said insulation film and connected to said microheater through contact holes;

an electrode formed on a portion of said insulation film and indirectly heated by said microheater; and a protection film formed on said electrode, said wirings and said insulation film, and patterned to expose a portion of said electrode and wirings.

2. The microelectrode of claim 1, wherein said microheater consists of any one of platinum and doped polysilicon.

3. The microelectrode of claim 1, wherein the inside of said cavity is maintained to be vacuum.

4. The microelectrode of claim 1, wherein said electrode is formed of any one of platinum and material including platinum.

5. The microelectrode of claim 1, wherein said electrode is formed as an IDA structure.

6. The microelectrode of claim 1, further comprising a metal electrode formed on said electrode.

7. The microelectrode of claim 6, wherein said electrode is formed as an IDA structure.

8. The microelectrode of claim 6, wherein the area of said metal electrode is larger than that of said cavity.

9. The microelectrode of claim 1, further comprising at least one additional electrode.

10. The microelectrode of claim 9, wherein on the top of said plurality of electrodes is formed of one metal electrode.

11. The microelectrode of claim 1, wherein said protection film is patterned so that said electrode is less exposed than the area of said cavity.

12. The microelectrode of claim 1, wherein said wirings are formed of a material including aluminum.

13. A microelectrode array, wherein the microelectrode as claimed in any one of claims 1 to 12 is arranged in the shape of an array.

\* \* \* \* \*